(12) United States Patent
Shen et al.

(10) Patent No.: US 9,840,551 B2
(45) Date of Patent: Dec. 12, 2017

(54) BLOOD MARKERS FOR DIAGNOSING EPITHELIUM DERIVED CANCERS AND MONOCLONAL ANTIBODIES THEREOF

(71) Applicant: Beijing Cotimes Biotech Co., Ltd., Beijing (CN)

(72) Inventors: Enyun Shen, Beijing (CN); Yang Song, Beijing (CN); Shiqi Ren, Beijing (CN)

(73) Assignee: Beijing Cotimes Biotech Co. Ltd., Beijing (CN)

( * ) Notice: Subject to any disclaimer, the term of this patent is extended or adjusted under 35 U.S.C. 154(b) by 34 days.

(21) Appl. No.: 14/992,750

(22) Filed: Jan. 11, 2016

(65) Prior Publication Data

US 2016/0122423 A1 May 5, 2016

Related U.S. Application Data

(62) Division of application No. 13/821,844, filed as application No. PCT/CN2010/001387 on Sep. 9, 2010, now Pat. No. 9,255,142.

(51) Int. Cl.
| | |
|---|---|
| *C07K 16/18* | (2006.01) |
| *G01N 33/574* | (2006.01) |
| *C07K 16/30* | (2006.01) |
| *G01N 33/68* | (2006.01) |

(52) U.S. Cl.
CPC .............. *C07K 16/18* (2013.01); *C07K 16/30* (2013.01); *G01N 33/57423* (2013.01); *G01N 33/57496* (2013.01); *G01N 33/6893* (2013.01); *G01N 2333/4742* (2013.01)

(58) Field of Classification Search
CPC .. C07K 16/18; C07K 16/30; G01N 233/4742; G01N 33/574–33/57484
See application file for complete search history.

(56) References Cited

U.S. PATENT DOCUMENTS

| | | | |
|---|---|---|---|
| 5,288,614 | A | 2/1994 | Bodenmuller et al. |
| 9,255,142 | B2 * | 2/2016 | Shen ............... C07K 16/30 |
| 2008/0020414 | A1 | 1/2008 | Karl et al. |
| 2009/0176228 | A1 | 7/2009 | Birse et al. |

FOREIGN PATENT DOCUMENTS

| | | |
|---|---|---|
| CN | 1471587 A | 1/2004 |
| CN | 1544463 A | 11/2004 |
| CN | 1639185 A | 7/2005 |

OTHER PUBLICATIONS

Dohmoto et al., The Role of Caspase 3 in Producing Cytokeratin 19 Fragment (CYFRA21-1) in Human Lung Cancer Cell Lines, Int. J. Cancer, vol. 91, 2001, pp. 468-473.
English translation of International Search Report on International Application No. PCT/CN2010/001387 dated Jun. 16, 2011, (7 pages).
Fan, Z.F., et al., "Research and Clinical Evaluation of Tumor Markers", Labeled Immunoassays and Clinical Medicine, (2002), vol. 9, No. 2, pp. 108-111, (in Chinese).
Final Office Action on U.S. Appl. No. 13/821,844, dated Jun. 24, 2015.
Linder, Stig, et al., "Determining tumor apoptosis and necrosis in patient serum using cytokeratin 18 as a biomarker", Cancer Letters, (2004), vol. 214, No. 1, pp. 1-9, Elsevier.
Nap, M., et al., "Immunohistochemical Profiles of 30 Monoclonal Antibodies against Cytokeratins 8, 18 and 19", Tumor Biology, (2001), vol. 22, No. 1, pp. 401310, S. Karger AG.
Niklinski, J., et al., "Preoperative CYFRA 21-1 level as a prognostic indicator in resected nonsmall cell lung cancer", European Respiratory Journal, (1998), vol. 12, No. 6, pp. 1424-1428, European Respiratory Society.
Non-Final Office Action on U.S. Appl. No. 13/821,844, dated Mar. 4, 2015.
Notice of Allowance on U.S. Appl. No. 13/821,844, dated Oct. 1, 2015.
Stigbrand et al., Tumor Biol, 1998, vol. 19, pp. 132-162.
Stigbrand, T., "The Versatility of Cytokeratins as Tumor Markers", Tumor Biology, (2001), vol. 22, No. 1, pp. 1-3, S. Karger AG.

* cited by examiner

*Primary Examiner* — Jessica H Roark
(74) *Attorney, Agent, or Firm* — Foley & Lardner LLP

(57) ABSTRACT

The present invention provides uses of cytokeratins as markers for diagnosing epithelium derived cancers. The present invention provides cancer-related epitopes of cytokeratins and monoclonal antibodies which specifically recognize the epitopes. The present invention also provides methods for the early screen, diagnosis or prognosis of epithelium derived cancers in subjects, methods for the evaluation of therapeutic effect of related medicaments or therapies, and kits for accomplishing the methods.

16 Claims, 9 Drawing Sheets

1: GY12 cDNA
2: GY11 cDNA
3: GY10 cDNA
4: Marker

1: TOPO-GY10;
2: TOPO-GY11;
3: TOPO-GY12;
4: Digested TOPO-GY10;
5: Digested TOPO-GY11;
6: Digested TOPO-GY12;
M: Marker.

1: GY22cDNA
2: GY21cDNA
3: GY20cDNA
4: Marker

1: TOPO-GY20;
2: TOPO-GY21;
3: TOPO-GY22;
4: Digested TOPO-GY20;
5: Digested TOPO-GY21;
6: Digested TOPO-GY22;
M: Marker.

M: Marker
1: Recombinant Cytokeratin 19 fragement GY20
2: Recombinant Cytokeratin 19 fragement GY21
3: Recombinant Cytokeratin 19 fragement GY22

SEQUENCE LISTING

<160> NUMBER OF SEQ ID NOS: 6

<210> SEQ ID NO 1
<211> LENGTH: 430
<212> TYPE: PRT
<213> ORGANISM: Homo sapiens

<400> SEQUENCE: 1

```
Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Ser Gly Ser Arg Ile Ser Val
            35                  40                  45

Ser Arg Ser Thr Ser Phe Arg Gly Gly Met Gly Ser Gly Gly Leu Ala
        50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
                100                 105                 110

Arg Glu His Leu Glu Lys Lys Gly Pro Gln Val Arg Asp Trp Ser His
            115                 120                 125

Tyr Phe Lys Ile Ile Glu Asp Leu Arg Ala Gln Ile Phe Ala Asn Thr
130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
        195                 200                 205

Glu Leu Leu Phe Met Lys Lys Asn His Glu Glu Val Lys Gly Leu
    210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
            260                 265                 270

Gln Gln Ile Glu Glu Ser Thr Thr Val Val Thr Thr Gln Ser Ala Glu
        275                 280                 285

Val Gly Ala Ala Glu Thr Thr Leu Thr Glu Leu Arg Arg Thr Val Gln
```

```
                290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
                340                 345                 350

Arg Ala Glu Gly Gln Arg Gln Ala Gln Glu Tyr Glu Ala Leu Leu Asn
            355                 360                 365

Ile Lys Val Lys Leu Glu Ala Glu Ile Ala Thr Tyr Arg Arg Leu Leu
        370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
            420                 425                 430

<210> SEQ ID NO 2
<211> LENGTH: 51
<212> TYPE: PRT
<213> ORGANISM: Homo sapiens

<400> SEQUENCE: 2

Glu Thr Glu Ile Glu Ala Leu Lys Glu Glu Leu Leu Phe Met Lys Lys
1               5                   10                  15

Asn His Glu Glu Val Lys Gly Leu Gln Ala Gln Ile Ala Ser Ser
            20                  25                  30

Gly Leu Thr Val Glu Val Asp Ala Pro Lys Ser Gln Asp Leu Ala Lys
        35                  40                  45

Ile Met Ala
    50

<210> SEQ ID NO 3
<211> LENGTH: 51
<212> TYPE: PRT
<213> ORGANISM: Homo sapiens

<400> SEQUENCE: 3

Ala Gln Thr Arg Ala Glu Gly Gln Arg Gln Ala Gln Glu Tyr Glu Ala
1               5                   10                  15

Leu Leu Asn Ile Lys Val Lys Leu Glu Ala Glu Ile Ala Thr Tyr Arg
            20                  25                  30

Arg Leu Leu Glu Asp Gly Glu Asp Phe Asn Leu Gly Asp Ala Leu Asp
        35                  40                  45

Ser Ser Asn
    50

<210> SEQ ID NO 4
<211> LENGTH: 400
<212> TYPE: PRT
<213> ORGANISM: Homo sapiens

<400> SEQUENCE: 4

Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30
```

Ala Pro Ser Ile His Gly Gly Ser Gly Gly Arg Gly Val Ser Val Ser
                35                  40                  45

Ser Ala Arg Phe Val Ser Ser Ser Ser Gly Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
                100                 105                 110

Arg Asp Trp Tyr Gln Lys Gln Gly Pro Gly Pro Ser Arg Asp Tyr Ser
                115                 120                 125

His Tyr Tyr Thr Thr Ile Gln Asp Leu Arg Asp Lys Ile Leu Gly Ala
                130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Gln Ala Leu Arg
                165                 170                 175

Met Ser Val Glu Ala Asp Ile Asn Gly Leu Arg Arg Val Leu Asp Glu
                180                 185                 190

Leu Thr Leu Ala Arg Thr Asp Leu Glu Met Gln Ile Glu Gly Leu Lys
                195                 200                 205

Glu Glu Leu Ala Tyr Leu Lys Lys Asn His Glu Glu Glu Ile Ser Thr
210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
                260                 265                 270

Ser Arg Thr Glu Glu Leu Asn Arg Glu Val Ala Gly His Thr Glu Gln
                275                 280                 285

Leu Gln Met Ser Arg Ser Glu Val Thr Asp Leu Arg Arg Thr Leu Gln
                290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
                340                 345                 350

Arg Ala Asp Ser Glu Arg Gln Asn Gln Glu Tyr Gln Arg Leu Met Asp
                355                 360                 365

Ile Lys Ser Arg Leu Glu Gln Glu Ile Ala Thr Tyr Arg Ser Leu Leu
                370                 375                 380

Glu Gly Gln Glu Asp His Tyr Asn Asn Leu Ser Ala Ser Lys Val Leu
385                 390                 395                 400

<210> SEQ ID NO 5
<211> LENGTH: 26
<212> TYPE: PRT
<213> ORGANISM: Homo sapiens

<400> SEQUENCE: 5

Gln Glu Ile Ala Thr Tyr Arg Ser Leu Leu Glu Gly Gln Glu Asp His

-continued

```
1               5               10              15
Tyr Asn Asn Leu Ser Ala Ser Lys Val Leu
            20              25

<210> SEQ ID NO 6
<211> LENGTH: 26
<212> TYPE: PRT
<213> ORGANISM: Homo sapiens

<400> SEQUENCE: 6

Ala Glu Thr Glu Ala Arg Phe Gly Ala Gln Leu Ala His Ile Gln Ala
1               5                   10                  15

Leu Ile Ser Gly Ile Glu Ala Gln Leu Gly
            20                  25
```

BLOOD MARKERS FOR DIAGNOSING EPITHELIUM DERIVED CANCERS AND MONOCLONAL ANTIBODIES THEREOF

CROSS-REFERENCE TO RELATED APPLICATIONS

This Application is a Divisional of U.S. application Ser. No. 13/821,844, filed May 31, 2013, which is the U.S. National Stage of PCT/CN2010/001387, filed Sep. 9, 2010, the entire contents of which is incorporated herein by reference.

TECHNICAL FIELD

The present invention relates to cancer diagnosis. More specifically, the present invention relates to the use of cytokeratin fragments as markers for diagnosing epithelium-derived cancers.

BACKGROUND ARTS

For successful treatment of cancer patients, one of the most important factors is the early detection. With the development in gene analysis and proteomics, remarkable progress has been made in the identification of molecular markers for diagnosing and predicting specific cancers.

The epithelium-derived cancer refers to a cancer originated from the epithelial cell, and includes but is not limited to breast cancer, gastric cancer, oral cancer, esophageal cancer, colon cancer, liver cancer, bladder cancer, pancreatic cancer, ovarian cancer, cervix cancer, lung cancer, breast cancer and skin cancer, prostate cancer, renal cancer and the like.

For example, the gastric cancer is the second-leading cause of death by cancer in the world and one of the most common malignant tumors that threaten the human health. The key of the prognosis of gastric cancer patients is to make a good secondary prophylaxis, i.e. early finding and early treating. The early, timely and accurate detection and treatment of the gastric cancer have an important meaning in reducing the gastric cancer mortality.

Lung cancer is a common lung malignant tumor. In recent years, the morbidity and mortality of lung cancer rapidly increase due to the influences of smoking and various environmental factors in the world, especially in the industrially developed countries. The development of serum tumor markers having a high specificity and sensibility has an important meaning for the early finding and treating of lung cancer.

Molecular diagnosis is the most popular method of diagnosing cancer. Different kinds of molecules such as DNA, protein, and fat are used as diagnosis tools. Tumor markers (TM) refer to a group of substances that are produced or secreted by tumor cells and released into blood, cells and body fluid in the process of tumorigenesis and proliferation, which reflect the presence and growth of tumors. Tumor markers are generally proteins, and are widely used in the detection and diagnosis of various types of cancers. The increase of tumor marker concentration may indicate that a cancer is present in the human body in a certain form. Tumor markers are clinically used in the finding of primary tumors, the screening of tumor high risk population, the differential diagnosis of benign and malignant tumors, the determination of tumor development level, the observation and evaluation of tumor therapeutic effect, the predicting of tumor relapse and prognosis, and the like. Tumor markers are generally measured by immunoassay methods, such as indirect method, double antibody sandwich method, and competitive method. The detection methods include colloidal gold method, enzyme-linked immunosorbent assay, chemiluminescent assay, electrochemiluminescence assay and the like. The object of serological detection is to determine the contents of cancer-related tumor markers in patient's serum. This method is simple and practicable, and therefore is suitable for the extensive survey in a large population. For example, the gastric cancer-related tumor markers that are currently widely used internationally include CEA, TPS and CA72-4, and the like.

Cytokeratins include over 20 different proteins, and are important constituents of cytoskeleton. Although all of the cells with an epithelium origin express a certain level of cytokeratin, certain constituents of keratin such as keratins 8, 18 and 19 have an intimate relationship with the genesis and development of malignant tumors (M. Nap, Th. Van Wel, C. Andres, et al. Immunohistochemical Profiles of 30 Monoclonal Antibodies against Cytokeratins 8, 18 and 19[J]. Tumor Biology 2001; 22:4-10).

Cytokeratin 18 is an acidic protein having a molecular weight of 55 kD, consists of 430 amino acids, has a highly conservative center region with an alpha helix structure, and shows a filament-like structure. It is widely distributed in normal tissue surfaces, such as stratified epithelium and squamous epithelium, and monolayer epithelial cells such as acinus, trachea, mammary duct, sweat gland, endometrium, colon and hepatic cell. In normal epithelial cells, the expression of cytokeratin 18 is relatively stable. There is no or low expression of cytokeratin 18 and its fragments in peripheral blood, marrow, and lymph node. Almost no fragments are released into blood. On the contrary, in case of malignant transformation of epithelial cells, the expression of cytokeratin 18 sharply increases. In the meanwhile, the growth of cytokeratin 18 becomes abnormal. The protease activated in the apoptosis and necrosis of tumor cells accelerates cell degradation, which allows many soluble cytokeratin 18 fragments to be released, and causes the concentration of soluble cytokeratin 18 fragments in tissue fluid and body fluid (in particular in the blood circulation of patients having gastric cancer) to increase (Stig L, Aleksandra M H, Takayuki U, et al. Determining tumor apoptosis and necrosis in patient serum using cytokeratin 18 as a biomarker[J]. Cancer Letters 214(2004):1-9; T. Stigbrand. The Versatility of Cytokeratins as Tumor Markers[J]. Tumor Biology 2001; 22:1-3).

Cytokeratin 19 is an acidic protein having a molecular weight of 40 kD, the smallest member in the keratin family, consists of 400 amino acids, has a highly conservative center region with an alpha helix structure, and shows a filament-like structure. It is widely distributed in normal tissue surfaces, such as stratified epithelium and squamous epithelium, and monolayer epithelial cells such as acinus, trachea, mammary duct, sweat gland, endometrium, colon and hepatic cell. In normal epithelial cells, the expression of cytokeratin 19 is relatively stable. There is no or low expression of cytokeratin 19 and its fragments in peripheral blood, marrow, and lymph node. Almost no fragments are released into blood circulation system. On the contrary, in case of malignant transformation of epithelial cells, the expression of cytokeratin 19 sharply increases. In the meanwhile, the growth of cytokeratin 19 becomes abnormal. The protease activated in the apoptosis and necrosis of tumor cells accelerates cell degradation, which allows many soluble cytokeratin 19 fragments to be released, and causes the concentration of the soluble cytokeratin 19 fragments in tissue fluid and body fluid (in particular in blood circulation of patients having lung cancer) to increase (J. Niklinski, T. Burzykowski, W. Niklinska, et al. Preoperative CYFRA 21-1 level as a prognostic indicator inresected nonsmall cell lung cancer [J]. Eur Respir J 1998; 12: 1424-1428).

SUMMARY OF THE INVENTION

In an aspect, the present invention provides an epithelium-derived cancer related cytokeratin fragment, wherein the fragment contains an epitope selected from the group consisting of SEQ ID NOs: 2, 3, 5 and 6. In an embodiment, the fragment contains amino acid residues 200-400 of SEQ ID NO: 1. In another embodiment, the fragment contains amino acid residues 325-400 of SEQ ID NO: 2.

In another aspect, the present invention provideds a monoclonal antibody that specifically binds the epitope. In an embodiment, the monoclonal antibody is generated from a hybridoma having a deposit number of CGMCC No. 1957, CGMCC No. 1956, CGMCC No. 1955 or CGMCC No. 1952.

The present invention further provides an antigen-binding moiety of the monoclonal antibody, wherein the antigen-binding moiety competitively binds the epitope with the monoclonal antibody. In an embodiment, the antigen-binding moiety is a humanized antibody. In another embodiment, the antigen-binding moiety is a chimeric antibody.

In one aspect, the present invention provides a method of early screening, diagnosing or prognostically evaluating an epithelium-derived cancer in a subject, wherein the method comprises obtaining a biological sample from the subject, detecting the content of the cytokeratin fragment of the present invention in the biological sample, and comparing the content with a threshold level. If the content is higher than the threshold level, it is indicated that the subject may have a cancer.

In a preferred embodiment, the method further relates to the combination with other epithelium-derived tumor markers. In particular, the method comprises obtaining a biological sample from the subject, detecting the content of the cytokeratin fragment of the present invention in the biological sample, detecting the content of other epithelium-derived tumor markers in the biological sample, and comparing the contents of the cytokeratin fragment and the other epithelium-derived tumor markers with threshold levels. Preferably, the other epithelium-derived tumor marker is selected from the group consisting of AFP, CEA, CA242, CA19-9, CA72-4, CA125, CA15-3, NSE, SCCA, Cyfra21-1, PSA and free PSA.

In another aspect, the present invention provides a method of evaluating the therapeutic effect of a medicament or therapy for treating an epithelium-derived cancer, which comprises administering the medicament or therapy to a subject having the epithelium-derived cancer, collecting biological samples of the subject before and after administering the medicament or therapy, and detecting the content of the cytokeratin fragment of the present invention in the biological samples, wherein if the content of the cytokeratin fragment is substantially decreased after administering the medicament or therapy in comparison with before administering the medicament or therapy, it is indicated that the medicament or therapy has a remarkable therapeutic effect.

Preferably, the epithelium-derived cancer is selected from the group consisting of gastric cancer, liver cancer, lung cancer, gallbladder cancer, breast cancer, cervix cancer, ovarian cancer, colon cancer, prostate cancer, renal cancer, esophageal cancer, intestinal cancer, bladder cancer.

Preferably, the biological sample is selected from the group consisting of blood, serum, tissue fluid, urine, excrement, sputum, cerebrospinal fluid, saliva, tear and nipple aspirate fluid.

In another aspect, the present invention provides a kit, which comprises a coating antibody immobilized on a solid phase support and capable of specifically binding the cytokeratin fragment of the present invention, and a detecting antibody labelled detectably and capable of specifically binding the cytokeratin fragment. The kit can be used to apply the method of the present invention, and can be used to detect the cytokeratin fragment of the present invention.

The present invention further provides the use of a specific binder of the cytokeratin fragment, such as the monoclonal antibody or the antigen-binding moiety of the present invention in the manufacture of an agent for diagnosing an epithelium-derived cancer.

BRIEF DESCRIPTION OF RELEVANT SEQUENCES

Figure 1:
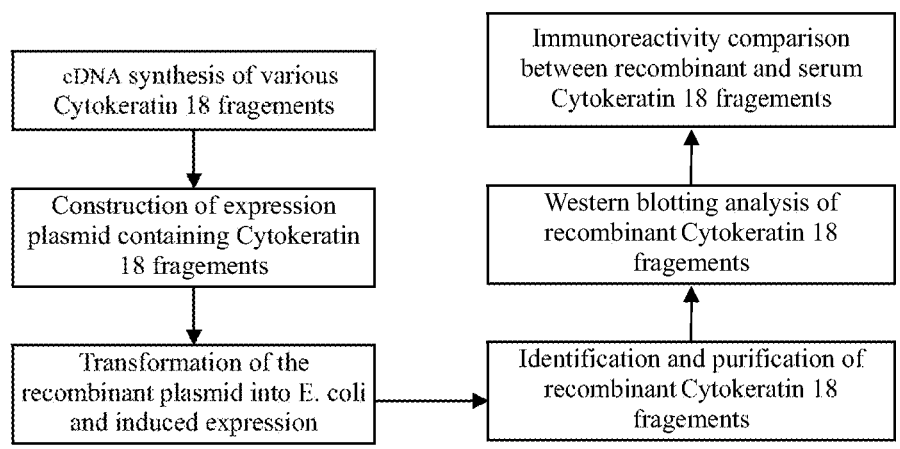
FIG. 1 is a flow chart, briefly describing the steps of preparing the cytokeratin 18 fragments and analyzing their activities.

SEQ ID NO:1 shows the full-length amino acid sequence of cytokeratin 18 (K18 for short), having a length of 430 amino acid residues.

SEQ ID NO:2 shows the amino acid sequence of the K18 epitope identified by monoclonal antibody 3A9, having a length of 51 amino acid residues, and corresponding to amino acid positions 200-250 of SEQ ID NO:1.

SEQ ID NO:3 shows the amino acid sequence of the K18 epitope identified by monoclonal antibody 2A6, having a length of 51 amino acid residues, and corresponding to amino acid positions 350-400 of SEQ ID NO:1.

SEQ ID NO:4 shows the full-length amino acid sequence of cytokeratin 19 (K19 for short), having a length of 400 amino acid residues.

SEQ ID NO:5 shows the amino acid sequence of the K19 epitope identified by monoclonal antibody 2G2, having a length of 26 amino acid residues, and corresponding to the amino acid positions 375-400 of SEQ ID NO:4.

SEQ ID NO:6 shows the amino acid sequence of the K19 epitope identified by monoclonal antibody 5H2, having a length of 26 amino acid residues, and corresponding to the amino acid positions 325-350 of SEQ ID NO:4.

DETAILED DESCRIPTION OF THE INVENTION

The present invention provides two epithelium-derived cancer related epitopes of cytokeratin 18 (K18). These two cancer-related epitopes are located at the C-terminal of the amino acid sequence of cytokeratin 18, and their sequences are shown as SEQ ID NOs: 2 and 3. During malignant transformation, in particular during the malignant transformation of tissues such as stomach, colon, mammary gland, ovary, and kidney, the epitopes become exposed. The exposure of the cancer-related epitopes is accomplished by the continual proliferation, necrosis, apoptosis of tumor cells to release cytokeratin 18 fragments into blood. In normal tissues and in the blood of healthy humans, there is no expression of these two cancer-related epitopes. The present invention provides two monoclonal antibodies 3A9 and 2A6 that identify these two cancer-related epitopes respectively and these two monoclonal antibodies were used to invent the method of diagnosing cancer. The hybridoma used to produce K18 monoclonal antibodies 3A9 and 2A6 were deposited in China General Microbiological Culture Collection Center (CGMCC, No. 13, Zhongguancun North 1st Alley, Haidian, Beijing) on Mar. 8, 2007 under deposit numbers of CGMCC NOs. 1957 and 1956. The contents in the deposit certificates are incorporated herein by reference and are considered as a part of the original disclosure of the present invention.

The present invention also provides two epithelium-derived cancer-related epitopes of cytokeratin 19. Their sequences are shown as SEQ ID NOs: 5 and 6. The present invention provides two monoclonal antibodies 3A9 and 2A6 that identify these two cancer-related epitopes respectively and these two monoclonal antibodies were used to invent the method of diagnosing cancer. The hybridoma used to produce K19 monoclonal antibodies 2G2 and 5H2 were deposited in China General Microbiological Culture Collection Center (CGMCC, No. 13, Zhongguancun North 1st Alley, Haidian, Beijing) on Mar. 8, 2007 under deposit numbers of CGMCC NOs. 1955 and 1952. The contents in the deposit certificates are incorporated herein by reference and are considered as a part of the original disclosure of the present invention.

In an aspect, the present invention provides an epithelium-derived cancer-related cytokeratin fragment, wherein the fragment contains an epitope selected from the group consisting of SEQ ID NOs: 2, 3, 5 and 6.

As used herein, the term "epithelium-derived cancer" refers to a cancer derived from epithelial cells, including but not limited to breast cancer, basal cell carcinoma, adenocarcinoma, gastrointestinal cancer, cheilocarcinoma, oral cancer, esophageal cancer, small intestine cancer and gastric cancer, colon cancer, liver cancer, bladder cancer, pancreatic cancer, ovarian cancer, cervix cancer, lung cancer, breast cancer and skin cancer such as squamous cell carcinoma and basal cell carcinoma, prostate cancer, renal cell carcinoma and other cancers which are known to affect epithelial cells by the body.

As used herein, the term "fragment" refers to an amino acid sequence that lacks one or more amino acid residues in comparison with the native full-length protein. For example, the protein fragment can be obtained by deleting some residues from a full-length protein. For example, an N-terminal truncated fragment can be obtained by deleting some amino acid residues at the N-terminal of the protein.

The protein fragment can also contain a foreign sequence to form a chimeric protein fragment. For example, protein A, after the N-terminal domain thereof is deleted, may be attached to the N-terminal domain of protein B to form a chimeric fragment of protein A and protein B. It can be understood by a skilled person in the art that the chimeric fragment may have a length higher than that of protein A.

To facilitate the purification, a commonly used purification tag, such as GST (glutathion S-transferase) and His-tag (hexahistine) can be added into the protein fragment.

The cytokeratin fragment of the present invention may contain a continuous amino acid sequence near the epitope.

For example, the K18 fragment of the present invention can contain at least 60, 70, 80, 90, 100, 120, 150, 180, 200, 210, 220, 250, 280, 300, 320, 350, 380, 400 or 420 continuous amino acid residues of SEQ ID NO:1 that cover the epitope as represented in SEQ ID NO:2 or 3. For example, in an embodiment of the present invention, the K18 fragment contains amino acid residues 1-250 of SEQ ID NO: 1 covering the epitope identified by monoclonal antibody 3A9. In another embodiment, the K18 fragment contains amino acid residues 250-430 of SEQ ID NO: 1 covering the epitope identified by monoclonal antibody 2A6. In yet another embodiment, the K18 fragment contains amino acid residues 150-430 of SEQ ID NO: 1 simultaneously covering the two epitopes. A fragment containing one or two epitopes of K18 can be fused with an epitope of K19 to form a chimeric fragment.

The K19 fragment of the present invention can contain at least 30, 50, 60, 70, 80, 90, 100, 120, 150, 180, 200, 210, 220, 250, 280, 300, 320, 350 or 380 continuous amino acid residues of SEQ ID NO:4 covering the epitope as represented in SEQ ID NO:5 or 6. For example, in an embodiment of the present invention, the K19 fragment contains amino acid residues 1-375 of SEQ ID NO: 4 covering the epitope identified by monoclonal antibody 5H2. In another embodiment, the K19 fragment contains amino acid residues 150-400 of SEQ ID NO: 1 simultaneously covering the epitopes identified by monoclonal antibodies 2G2 and 5H2.

Protein fragments containing specific amino acid residues can be easily prepared by molecular cloning technology well known in the art.

As used herein, the term "biological sample" refers to a sample of biological material obtained from a subject (preferably a patient), including a tissue sample, a cell sample (for example, a biopsy sample, such as an aspiration biopsy sample, brush biopsy sample, surface biopsy sample, aspiration-needle biopsy sample, punch biopsy sample, excisional biopsy sample, open biopsy sample, incisional biopsy sample or endoscopic biopsy sample) and a tumor sample. The biological sample can also be a biological fluid sample. In a preferred embodiment, the biological sample is serum. However, blood, urine, saliva, cerebrospinal fluid, nipple aspirate fluid, supernatant of cell lysis and the like can also be used.

As described herein, the level of the cytokeratin fragment of the present invention can be measured with any means known by the skilled person in the art. According to the present invention, it is generally preferable to detect the level of the cytokeratin fragment in the biological sample with the antibody or the antigen-binding moiety of antibody. However, other methods can also be used. For example, the expression of the cytokeratin fragment can be measured by analysis of the mRNA transcript.

The method for evaluating mRNA level is well known in the art. For example, the detection of RNA transcript can be accomplished by Northern blotting method, wherein RNA preparation is conducted on a modified agarose gel, and the RNA preparation is transferred to a suitable support, such as active cellucose membrane, cellucose nitrate membrane, glass membrane or nylon membrane. Then a labeled (e.g. radiolabeled) cDNA or RNA is hybridized with the preparation, and the resulting material is washed and analyzed, for example, by radioautography. Alternatively, the expression of mRNA can be detected on a DNA matrix, chip or micro-matrix. For example, in order to monitor the mRNA level, mRNA is extracted from the biological sample to be measured, and is subject to reverse transcription to produce a fluorescently labeled cDNA probe. Then, a micromatrix capable of being hybridized with the cytokeratin fragment cDNA is detected with the labeled cDNA probe, the glass slide is scanned, and the fluorescence intensity is measured. The fluorescence intensity is relevant to the hydridization intensity and the expression level.

The cytokeratin fragment level can also be measured, in particular when the biological sample is a fluid sample such as blood or urine. In an embodiment, the biological sample is contacted with a monoclonal antibody specifically binding the cytokeratin fragment to measure the cytokeratin fragment level.

The term "antigen-binding moiety of antibody" includes an immunoglobulin molecule or an immunologic competence determinant of the immunoglobulin molecule that specifically binds (immunologically reacts with) the epitope of the cytokeratin, such as a molecule that contains an antigen-binding site. The term "antigen-binding moiety of antibody" is intended to include a full antibody, for example, any isotype (IgG, IgA, IgM, IgE, and the like), and also include an antibody fragment. The antibody fragmentation can be conducted with a conventional technique. Therefore, this term includes a proteolytic fragment or a recombinantly prepared moiety of the antibody molecule that can selectively react with a certain protein. Non-limiting examples of these proteolytic and/or recombinant fragments include Fab, F(ab')$_2$, Fab', Fv, dAbs and a single-chain antibody (scFv) that contains VL and VH domains linked with a polypeptide linker. The scFv can be covalently or non-covalently connected to form an antibody containing two or more binding sites. Therefore, the "antigen-binding moiety of antibody" includes polyclonal antibody, monoclonal antibody or other purified preparation of antibody, and recombinant antibody. The term "antigen-binding moiety of antibody" also comprises a humanized antibody, a dual specific antibody and a chimeric molecule that contains at least one antigen-binding determinant derived from an antibody molecule. The term "humanized antibody" refers to an antibody, which is derived from a non-human (e.g. murine) antibody, and remains or substantially remains the antigen-binding characteristic of the parent antibody, but has a low immunogenicity in human. The advantage of humanized antibody is the reduction or elimination of immunogenicity of the antibody in the host, and therefore the increase of the bioavailability and the reduction of possible adverse immune reactions. The humanized antibody can be prepared by the CDR graft method.

As used herein, the term "labeled antibody" includes an antibody that is labeled in a detectable manner, including but not limited to an enzyme-labeled antibody, a radiolabeled antibody, a fluorescence-labeled antibody and a chemiluminescence-labeled antibody. A detectable-tag such as HA, HSV, FLAG or HIS labeled antibody can also be used.

In the diagnosis and prognosis method of the present invention, the antibody or the antigen-binding moiety of antibody is used to detect the level of the cytokeratin fragment. The level of the cytokeratin fragment present in the biological sample is relevant to the intensity of the signal emitted by the detectable labeled antibody.

In a preferred embodiment, an antibody can be bound to an enzyme to detectably label the antibody or the antigen-binding moiety of antibody. When the enzyme is contacted with its substrate, it will react with the substrate in such a manner that a detectable chemical moiety can be produced. For example, the detectable chemical moiety can be detected by spectrophotometry, fluorometry or visual observation. The enzyme that is useful for detectably labeling the antibody of the present invention includes but is not limited to malate dehydrogenase, horse radish peroxidase, alkaline phosphatase, asparaginase, glucose oxidase, urase, hydrogen peroxidase, glucoamylase and acetylcholine esterase. Chemiluminescence is another method useful for the detection of antibody or antigen-binding moiety thereof.

The detection can also be accomplished by any one of other immune assays. For example, an antibody can be detected by radiolabeling the antibody and then using the radioimmunoassay. For example, the radioisotope can be detected by using gamma counter or scintillation counter, or by the means of radioautography.

Labeling the antibody with a fluorescent compound is also feasible. When the fluorescence-labelled antibody is exposed to a light with suitable wavelength, its presence can be detected due to the fluorescence. Commonly used fluorescent compounds comprise fluorescein isothiocyanate, rhodamine, phycoerythrin and fluorescamine.

In an aspect of the present invention, there is provided a method of early screening, diagnosing or prognostically evaluating an epithelium-derived cancer in a subject, wherein the method comprises: obtaining a biological sample from the subject, detecting the content of the cytokeratin fragment in the biological sample, and comparing the content with a threshold level. If the content is higher than the threshold level, it is indicated that the subject may have a cancer or a bad prognosis.

In a preferred embodiment, the detection is conducted using the monoclonal antibody of the present invention. For example, only one monoclonal antibody can be used to detect the K18 or K19 fragment; 3A9 and 2A6 can be used in combination to detect the K18 fragment; 2G2 and 5H2 can be used in combination to detect the K19 fragment; 3A9 and 2G2 can also be used in combination to simultaneously detect the K18 fragment and the K19 fragment; or the above four monoclonal antibodies can be concurrently used in combination to conduct the detection. It should be understood that using several antibodies in combination can improve the accuracy of the diagnosis.

As used herein, the term "3A9" refers to the monoclonal antibody generated from hybridoma having a deposit number of CGMCC NO. 1957, which can specifically identify the epitope on K18.

As used herein, the term "2A6" refers to the monoclonal antibody generated from hybridoma having a deposit number of CGMCC NO. 1956, which can specifically identify the epitope on K18.

As used herein, the term "2G2" refers to the monoclonal antibody generated from hybridoma having a deposit number of CGMCC NO. 1955, which can specifically identify the epitope on K19.

As used herein, the term "5H2" refers to the monoclonal antibody generated from hybridoma having a deposit number of CGMCC NO. 1952, which can specifically identify the epitope on K19.

In a preferred embodiment, the present method further comprises the combined use with other epithelium-derived tumor markers, for example, commonly used tumor markers such as AFP, CEA, CA242, CA19-9, CA72-4, CA125, CA15-3, NSE, SCCA, Cyfra21-1, PSA, free PSA. The detection in which several tumor markers are combined can facilitate the improvement of diagnosis accuracy.

In another aspect of the present invention, there is provided a method of evaluating the therapeutic effect of a medicament or therapy for treating an epithelium-derived cancer, which comprises: administering the medicament or therapy to a subject having the epithelium-derived cancer, collecting a biological sample of the subject before and after administering the medicament or therapy, and detecting the content of the cytokeratin fragment of the present invention in the biological sample, wherein if the content of the cytokeratin fragment is substantially decreased after administering the medicament or therapy in comparison with before administering the medicament or therapy, it is indicated that the medicament or therapy has a remarkable therapeutic effect.

The present invention also involves a commercial kit for conducting the detection and prognosis evaluation of an epithelium-derived cancer. Said kit may be in any arrangement that are well known by the skilled person in the art to conduct one or more methods as described in the present invention. In addition, it is preferable to conduct the tests using one or more standard substances contained in the kit in the same time so as to quantitate or verify the test results. For example, the standard substance can be a purified K18 or K19 protein.

The kit comprises a means for detecting the level of cytokeratin fragment, for example, an antibody or an antibody fragment that selectively binds to the cytokeratin fragment. Preferably, the kit for the diagnosis and detection is arranged in a standard dual antibody combination, wherein one specific antibody is used to capture the cytokeratin fragment in the subject's sample, and the other specific antibody is used to detect the captured cytokeratin fragment. For example, the capturing antibody (coating antibody) is immobilized on a solid phase such as testing plate or cellucose nitrate membrane. Generally, a detectable label such as horse radish peroxidase or a radioisotope is used as a tag for the second antibody (i.e. detecting antibody).

In a preferred embodiment, 3A9 and 2A6 are used in combination in the kit to detect the K18 fragment. In another preferred embodiment, 2G2 and 5H2 are used in combination in the kit to detect the K19 fragment. 3A9 and 2G2 in combination can also be used to simultaneously detect the K18 fragment and the K19 fragment. Alternatively, the above four monoclonal antibodies in combination can be concurrently used to conduct the detection. It should be understood that using several antibodies in combination can improve the accuracy of the diagnosis.

In other embodiments, the detection kit may adopt the following techniques (but not limited to): competitive and non-competitive assay, radioactive immunoassay (RIA), bioluminescence and chemiluminescence assay, fluorometry, sandwich test, immunoradiometric assay, dot blot, enzyme-linked assay (including ELISA), microtiter plate and immunocytochemical method. For each kit, the test range, sensitivity, accuracy, reliability, specificity and reproducibility can be established by the methodologies well known to the skilled person in the art.

In the above detection kit, there is also provided an instruction for use.

The present invention is further illustrated by the following examples, which are provided as an aid in the understanding of the invention and are not construed as limitation thereto.

Example 1

1. The Preparation of Monoclonal Antibodies Against Keratin 18 and Its Fragments 1.1 the Preparation of Immunogen Recombinantcytokeratin 18 Fragment Recombinant cytokeratin 18 fragment GY10 was expressed in *E. coli* strain BL21 (DE3).

1.1.1 Research Scheme

See FIG. 1.

1.1.2 The Synthesis of cDNA of Cytokeratin 18 Fragment cDNAs encoding various cytokeratin 18 fragments were prepared by the RT-PCR method:

a) Template and Primer

Total RNAs were separated from a HELA human cancer cell line. Then, cDNAs were synthesized with the reverse transcription kit (Promega) according to its instruction. The obtained cDNAs were the templates for PCR. The primers were designed for three fragments, and each of cDNAs was subjected to the PCR amplification. Fragment numbers and amino acid sequences of the fragments were shown in Table 1-1.

TABLE 1-1

No. and amino acid sequence of recombinant cytokeratin 19 fragments

| No. of fragments | Amino acid sequence of cytokeratin 18 fragments |
|---|---|
| GY10 | aa1-430 |
| GY11 | aa150-430 |
| GY12 | aa180-430 | b) PCR Reaction

Components of PCR Reaction Solution:

cDNA template: 5 µl;
Primer: 5' and 3' primers, 10 pmol each
10×PCR buffer: 10 µl;
dNTP: 2.5 mM each, 4 µl in total;
Taq polymerase (Promega): 5 U;
Sterile double distilled water, added to 100 µl.

Figure 2:
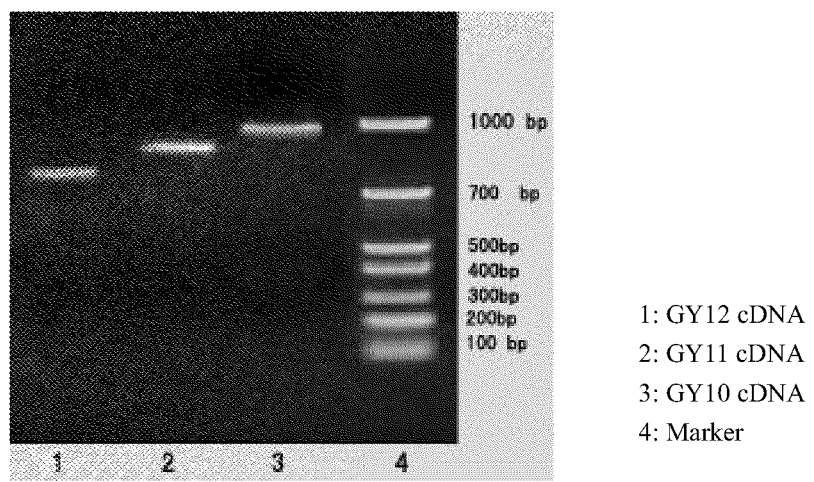
FIG. 2 is an electrophoretogram, showing the electrophoresis result of the cDNA of the cytokeratin 18 fragments.

The procedure was as follows:

The solution was heated to 94° C., kept constantly for 2 min, then run for 40 cycles, wherein each cycle was set as follows: heated at 94° C. for 30 s, at 52° C. for 1 min, and at 72° C. for 3 min. After that, the reaction solution was heated to 72° C. for 10 min. Then the amplified DNA fragment was collected, and separated with 1% agarose gel containing 0.25 µg/ml ethidium bromide (See FIG. 2). The result showed that the bands contained the cDNA fragments of the desired cytokeratin 18 fragments. Then the DNA fragments were recovered with Gene Clean kit (BIO101, Irvine, Calif.).

1.1.3 Plasmid Construction and Screening

The cDNA fragment was cloned with TOPO100 expression Cloning Kit (Invitrogen, Carlsbad, Calif.).

Figure 3:
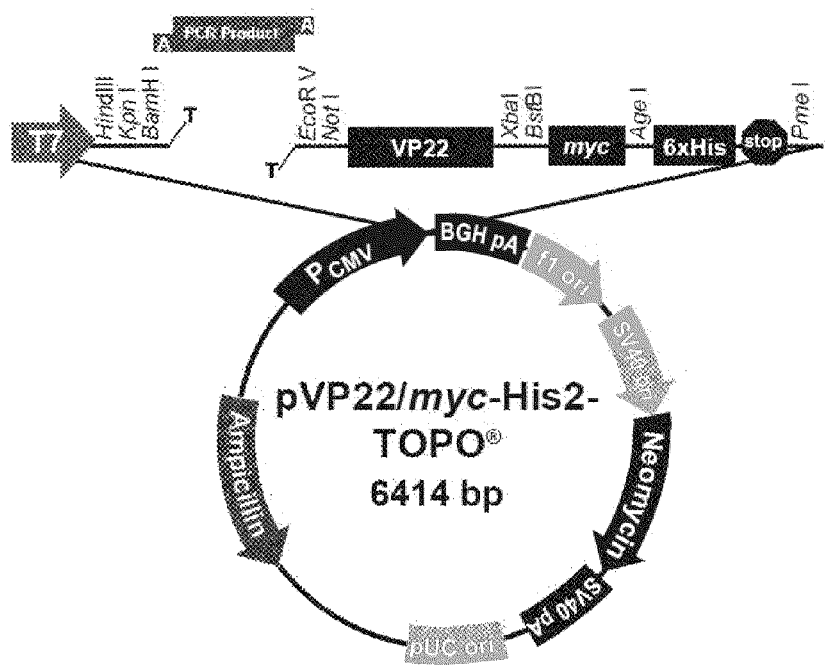
FIG. 3 shows the structure of the TOPO plasmid.

(1) The cDNA of cytokeratin 18 recovered from the PCR reaction solution and TOPO plasmid (FIG. 3) 50 ng provided from the cloning kit were mixed;

(2) To the solution was added 10× ligase reaction buffer (6 mM Tris-HCl (pH7.5), 6 mM MgCl, 5 mM NaCl, 7 mM β-mercaptoethanol, 0.1 mM ATP, 2 mM DTT, 1 mM spermidine, 0.1 mg/ml BSA);

(3) Then added 4 U T4 DNAligase (1 µl);

(4) The solution volume was adjusted with sterile deionized water to 10 µl;

(5) Incubated at 14° C. for 15 h;

(6) 2 µl was taken and added to 50 µl competent *E. coli* bacteria strain TOP10F (provided from TA cloning kit, and prepared into competence according to the instruction, the mixture was kept in an ice-bath for 30 min, then incubated at 42° C. for 30 s, and then in an ice-bath for 5 min)

(7) 500 µl of a medium was formulated, containing 2% (v/v) peptone, 0.5% (w/v) yeast extract, 0.05% (w/v) NaCl, 2.5 mM KCl, 1 mM MgCl and 20 mM glucose, (6) was added thereto, and incubated at 37° C. for 1 h in shaking.

(8) On the L-broth agar plate (1% (v/v) peptone, 0.5% (w/v) yeast extract, 0.5% (w/v) NaCl, 0.1% glucose, 0.6% (w/v) bacto-agar (Difo, Detroit, Mich.)) was plated (7), 100 µg/ml.

(9) The clones resistant to Ampicillin could be screened out from the medium surface, a single colony was picked out with a Pt-coated coil, put into the L-broth medium (containing Ampicillin 100 µg/ml), incubated at 37° C. overnight in shaking (200 rpm).

(10) After the incubation, the bacteria were collected by centrifugation, and the DNA plasmid was extracted with alkaline process.

Figure 4:
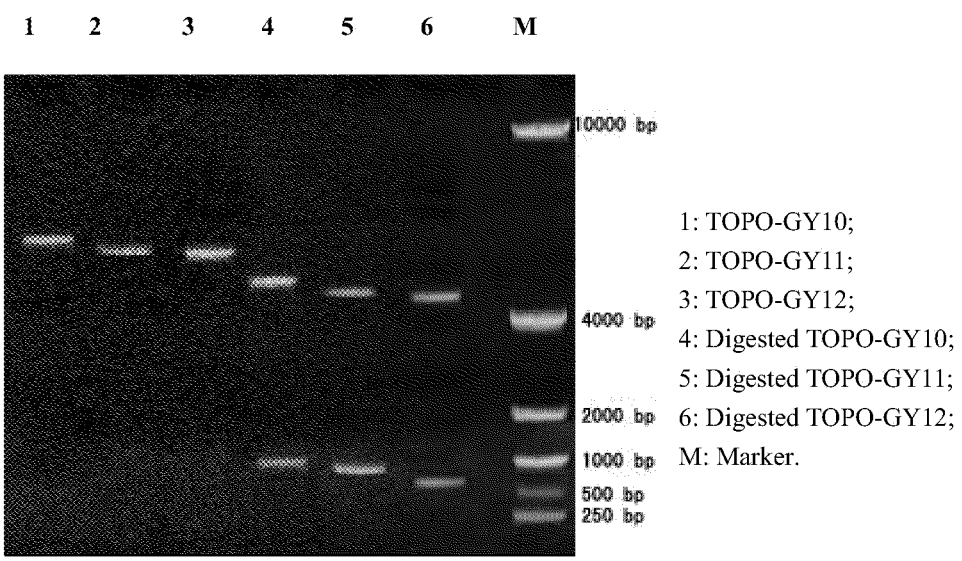
FIG. 4 is an electrophoretogram, showing the identification results of enzyme-digested recombinant expression plasmids TOPO-GY10, TOPO-GY11, and TOPO-GY12.

With the identification by enzyme digestion, the recombinant expression plasmids TOPO-GY10, TOPO-GY11, TOPO-GY12 had been obtained, as shown in FIG. 4.

1.1.4 Induced Expression and Identification of Recombinant Proteins cDNAs encoding various cytokeratin 18 had been inserted into TOPO plasmids, (1) The obtained plasmids were transformed into *E. coli* strain BL21 (DE3), then cultured in LB medium to the index growth phase, and the expression was induced with isopropanol-β-thiogalactoside (IPTG) for 3 h.

(2) The cells were precipitated, resuspended with lysis solution (8M urea, 20 mM Tris-HCl), and disrupted ultrasonically.

(3) After centrifuged at 14,000×g for 15 min, the supernatant was purified on the Ni column. The purified protein was dialyzed with a PBS solution and kept at 4° C. overnight.

(4) The protein concentration was detected with a BCA agent (Pierece, Woburn, Mass.).

1.1.5 Purification of Recombinant Cytokeratin 18

Sephadex G-50 was activated, and recombinant cytokeratin 18 fragments were purified with sieve chromatography. Sephadex G-50 was dissolved in 100 mM Tris-HCl buffer (pH 7.4), boiled at 100° C. for 10 minutes, then blocked with 100 mM Tris-HCl buffer (pH 7.4), and stored at 4° C. The concentrated solution of disrupted bacteria flowed through 2 ml gel beads at a flow rate of 2 ml/min. After passed, the sample was rinsed with 50 ml PBS, and elution buffer was 0.1 M glycine (pH 2.4), 0.15 M NaCl. The eluate was measured at ultraviolet OD280 nm and judged whether the elution was complete. The effective eluate (OD>0.01) was collected, put in a dialysis bag, and dialyzed with 1 L phosphate buffer (pH7.5) at 4° C., during which the dialysis buffer was exchanged twice. The purified protein was concentrated to about 1 mg/ml, added 1% NaN$_3$, and stored at 4° C. It was detected with 10% SDS-PAGE, and scanned and analyzed with the GDS8000 gel imaging system for the protein purity.

Figure 5:
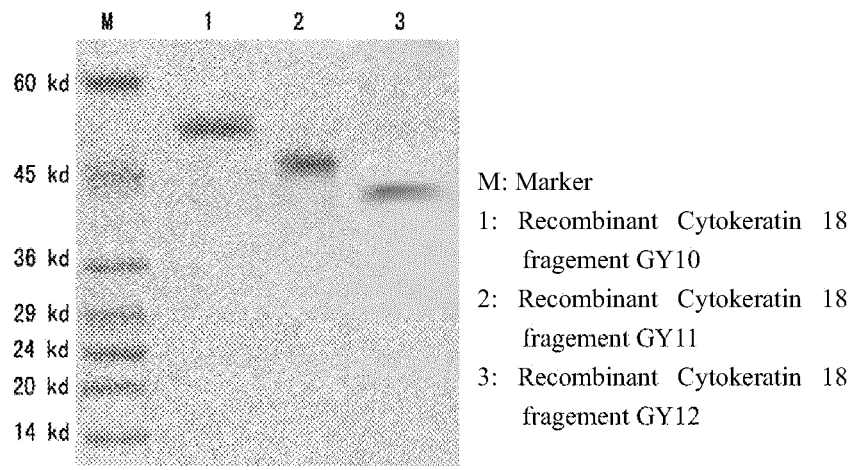
FIG. 5 is an electrophoretogram, showing the SDS-PAGE results of the recombinant cytokeratin 18 fragments GY10, GY11, and GY12.

The result was shown in FIG. 5. The result showed that high-purity recombinant cytokeratin 18 fragments GY10, GY11, and GY12 were obtained with an electrophoresis measured purity of over 95%.

The immunogen for preparing monoclonal antibodies was a full-length recombinant human cytokeratin 18, and this protein was bestowed by Prof. Zhou Tong, UAB university, US.

1.2 Immunization Procedure

Animal: 6-8 week-age female Balb/c mice.

Primary immunization (on Day 1): emulsified particles formed by evenly mixing 1 ml antigen protein solution and the same volume of Freund's complete adjuvant were used, with 100 µl plantar injection for each animal.

Secondary immunization (on Day 7): emulsified particles formed by evenly mixing 1 ml antigen protein solution and the same volume of Freund's incomplete adjuvant were used, with 100 µl plantar injection for each animal.

Enhanced immunization (on Days 14, 21 and 28): antigen (1 mg/ml) without any adjuvant was used, with 100 µl plantar injection for each animal.

Fusion (on Day 31).

1.3 Establishment of Hybridoma

Popliteal fossa and inguina of immuned mice were taken to separate lymphocytes which were mixed with NS1 myeloma cells at a ratio of 2:1. The mixture was washed with serum-free RPMI 1640 twice, and added 1 ml PEG1500 (preheated to 37° C.); the cells were mixed slightly at 37° C. for 1 min, then added dropwise slowly 20 ml serum-free RPMI 1640 medium (preheated to 37° C.) within 3 minutes. After centrifugation, the fused cells were suspended in 12% FBS RPMI 1640 HAT selective medium. Cells were put in five 96-well cell culture plates, 100 µl/well.

1.4 Screening Positive Clones by ELISA Assay

On Day 7 after the cell fusion, the primary screening was conducted by indirect ELISA method. All of the hybridomas were screened with three recombinant human cytokeratin 18 antigens: (1) full-length cytokeratin 18; (2) N-terminal cytokeratin 18 fragment; and (3) C-terminal cytokeratin 18 fragment.

The ELISA plates were coated with the above keratin 18 antigens (1 µg/ml) and kept at 4° C. overnight; washed with PBS three times, and blocked with PBS containing 3% (w/v) BSA at room temperature for 1 h. When detecting, 100 µl supernatant of the cell culture was added to each well; incubated at 37° C. for 30 min, washed with PBST washing solution for five times, after patting dry, peroxidase-conjugated goat antimouse immunoglobulin (HRP-GAM Ig, DAKO Company) was added, incubated at 37° C. for 30 min, after removing the plate from the incubator, washed with PBST washing solution for 5 times, after patting dry, added successively the substrate solution A and the developing solution B, 50 μl each (the components of the substrate solution A were: 13.42 g Na$_2$HPO$_4$.12H$_2$O, 4.2 g citric acid.H$_2$O and 0.3 g hydrogen peroxide, adjusted with deionized water to volume of 700 ml; the components of the developing solution B were: 0.2 g tetramethyl benzidine, 20 ml dimethylformamide adjusted with deionized water to volume of 700 ml), developed at 37° C. for 10 min, added 50 μl stop solution (2M H$_2$SO$_4$) to stop the reaction, and detected on the microplate reader for OD$_{450}$ values for each well, wherein those having a OD$_{450}$ value higher than 2.0 were regarded as positive.

The result of the primary screening of the monoclonal antibodies was summarized in Table 1-2. After detecting the supernatants resulted from the hybridoma culture in all of 480 wells with four antigens, the inventors identified that 48 clones had strong responses with the full-length cytokeratin 18 antigen, wherein 5 clones showed positive responses with the N-terminal and C-terminal fragments of keratin 18 and irrelevant control antigen, which were regarded as non-specific clones; wherein 18 clones showed positive responses with the N-terminal cytokeratin 18 fragments, and defined as N-terminal specific clones; wherein 24 clones showed positive responses with the C-terminal cytokeratin 18 fragments, and defined as C-terminal specific clones. In addition, one clone responded to the N-terminal and C-terminal antigens, and its response specificity was unknown. These N-terminal and C-terminal specific clones were used as candidates for further study.

These clones were subjected to three sub-clonings by the limiting dilution assay.

TABLE 1-2

The result of the primary screening for mouse anti-human keratin 18 monoclonal antibodies

| Response Result | | | | 480 clones in total the number of positive clones | Note |
| --- | --- | --- | --- | --- | --- |
| full-length keratin 18 | N-terminal fragment (aa1-250) | C-terminal fragment (aa200-430) | Negative control antigen | | |
| + | + | + | + | 5 | non-specific |
| + | + | − | − | 18 | N-terminal-specific |
| + | − | + | − | 24 | C-terminal-specific |
| + | + | + | − | 1 | unknown |

1.5 the Production and Purification of Monoclonal Antibodies 16 week-age healthy Balb/c mice were injected intraperitoneally with 0.5 ml pristane. 5-7 days later, colonized hybridoma cells were collected, centrifuged to remove the supernatant, added a serum-free medium, adjusted to cell density of $2 \times 10^5$-$2 \times 10^6$ cells/ml, each of mice was injected with 0.5 ml. 7-10 days later, the abdomen of mice enlarged, and the collection of ascites began. After centrifuging at 3000 rpm for 15 min, the intermediate pellucid liquid was taken, filtered with 0.45 μm micropore film to remove bacteria, separately packaged, and stored at −20° C.

The treated ascites was 5-fold diluted with 0.02 mol/L, pH7.4 PBS (81 ml 0.2 mol/L Na$_2$HPO$_4$, 19 ml 0.2 mol/L NaH$_2$PO$_4$, added to 100 ml with physiological saline). 50 ml supernatant was added to 2 ml protein-A/G chromatography column at a flow rate of 1 ml/min. Then the affinity chromatography column was washed with PBS until the effluent had an OD280 value of below 0.01. Then, the antibodies bound to the chromatography column were eluted with 0.1M Glycine-HCL buffer pH2.4, the eluted components were collected in 2 ml/tube, finally all of the eluted components having OD280 higher than 0.1 were mixed, then neutralized with 1/10 volume of 1M Tris-HCL pH 8.5 solution, and finally dialyzed overnight in the PBS solution, during which the dialysis buffer was exchanged twice.

1.6 the Preparation of Enzyme Labelled Antibody

The conventional method for labeling the monoclonal antibody and the polyclonal antibody with horse radish peroxidase (HRP) was sodium periodate method. Its principle was that the glycosyl of HRP was oxidized with sodium periodate to become an aldehyde group, after adding the antibody IgG, the aldehyde group bound with the amino of IgG to form a Schiff base. In order to prevent the aldehyde group of the saccharide in the HRP from coupling with the amino of the protein itself, the amino was blocked with dinitrofluorobenzene before the oxidation with sodium periodate. At the end of the oxidation reaction, the Schiff base was stabilized with sodium borohydride.

(1) Dissolving 5 mg HRP into 0.5 ml 0.1 mol/L NaHCO$_3$ solution; adding 0.5 ml 10 mmol/L NaIO$_4$ solution, mixing evenly, closing the lid tightly, keeping at room temperature in the darkness for 2 h.

(2) Adding 0.75 ml 0.1 mol/L Na$_2$CO$_3$ and mixing evenly.

(3) Adding 0.75 ml purified monoclonal antibody (15 mg/ml), and mixing evenly.

(4) Weighing Sephadex G25 dried powder 0.3 g, adding to the outer barrel of 5 ml syringe matted with glass cotton at the lower opening; then transferring the above conjugate into the syringe outer jacket; closing tightly, keeping at room temperature (in the darkness) for 3 h or at 4° C. overnight.

(5) Eluting all of the conjugate with a small amount of PBS, collecting the eluate, adding 1/20V-volumed fresh 5 mg/ml NaBH$_4$ solution, mixing evenly, keeping at room temperature for 30 min; then adding 3/20V NaBH$_4$ solution, mixing evenly, keeping at room temperature for 1 h (or at 4° C. overnight).

(6) Passing the conjugate through Sephadex G200 or Sepharose 6B (2.6×50 cm) to purify by chromatography, and collecting the first peak in separate tubes.

(7) Identifying the mass of enzyme conjugate:
Determination of Molar Ratio
Enzyme amount (mg/ml)=OD$_{403}$×0.4
IgG amount (mg/ml)=(OD$_{280}$−OD$_{403}$×0.3)×0.62
Molar ratio (E/P)=Enzyme amount×4/IgG amount, generally between 1 and 2.

Enzyme binding rate=enzyme amount×volume/antibodies. The labeling rate is generally 0.3-0.6, i.e. 1-2 HRP molecules may bind to one antibody molecule. The labeling rate can be higher than 0.6, 0.8, 0.9; When OD$_{403}$/OD$_{280}$ equals to 0.4, E/P is about 1.

The labeling rate=OD$_{403}$/OD$_{280}$

Determination of Enzyme Activity and Antibody Activity

The enzyme activity of the enzyme conjugate, antibody activity, titer and specificity could be determined by ELISA method, immunodiffusion, DAB-H$_2$O$_2$ chromogenic reaction.

(8) Preserving the HRP antibody conjugate: adding glycerol of the same amount, splitting into small amounts and keeping at −20° C. so as to avoid repeated freezing and thawing; or adding the same amount of 60% glycerol and keeping at 4° C.; it was not suitable to add NaN$_3$ or phenol for antisepsis, otherwise the enzyme activity would be compromised. If necessary, preserving under lyophilization, with BSA or skim milk as protector.

1.7 Screening of Tumor-Related Keratin 18 Fragments Monoclonal Antibody Pairs and Preliminary Clinical Verification After confirming the antigen reactivities of purified and enzyme labelled antibodies by the ELISA method, 10 strains of antibodies with high affinity were selected to conduct the paring test to screen out gastric cancer-highly related keratin 18 antibody pairs.

1.7.1 Cross-Pairing Test

In order to obtain monoclonal antibody pairs having selectivity to gastric cancer serum keratin 18, 10 gastric cancer serum samples and 10 normal human serum samples were taken as testing samples. 10 gastric cancer serum samples of the same volume were mixed as the positive sample. 10 normal human serum samples of the same volume were mixed as the negative sample. A 96-well plate was coated with 1 µg/ml purified antibody and kept at 4° C. overnight, and then blocked with a PBS containing 3% BSA at room temperature for 1 h. Then, to each well of one ELISA plate was added 50 µl of gastric cancer positive serum, and to each well of another ELISA plate was added the normal human negative control serum, and then 50 µl of 1:1000 enzyme labelled antibodies were added respectively. The plates were incubated at 37° C. and then washed, added a developing substrate, kept in the darkness for 10 min, added a stop solution, and measured for the OD value at 450 nm.

Table 1-3 summarized the cross-pairing test results for 5 pairs of monoclonal antibodies, wherein 3A9/2A6-HRP, 2A6/3A9-HRP, 3H7/3A9-HRP antibody pairs showed strong positive responses to gastric cancer serum and negative responses to normal human serum. Therefore, it was established that the serum keratin 18 detected by these antibody pairs are highly related to gastric cancer.

TABLE 1-3

Crossing test for screening gastric cancer-related keratin 18 antibody

|  | Gastric | Coating antibody | | | | |
| --- | --- | --- | --- | --- | --- | --- |
| Normal human | cancer | 2A6 | 2E6 | 2H6 | 3A9 | 3H7 |
| Enzyme-labeled antibody | 2A6 | 0.05 | 0.12 | 0.09 | 0.05 | 0.14 |
|  |  | 0.11 | 0.98 | 1.22 | 1.88 | 0.78 |
|  | 2E6 | 0.09 | 0.05 | 0.14 | 0.12 | 0.16 |
|  |  | 1.12 | 0.06 | 0.87 | 1.12 | 0.92 |
|  | 2H6 | 0.12 | 0.09 | 0.06 | 0.09 | 0.09 |
|  |  | 0.98 | 0.56 | 0.12 | 0.92 | 0.66 |
|  | 3A9 | 0.08 | 0.09 | 0.12 | 0.05 | 0.08 |
|  |  | 1.54 | 1.24 | 0.88 | 0.12 | 0.98 |
|  | 3H7 | 0.11 | 0.15 | 0.13 | 0.06 | 0.08 |
|  |  | 0.68 | 0.88 | 0.98 | 1.22 | 0.12 |

Figure 6:
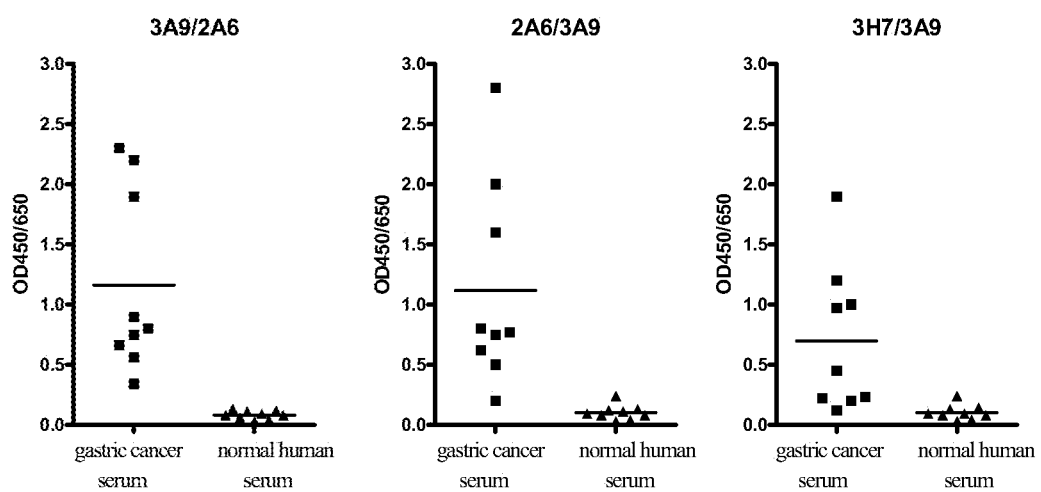
FIG. 6 shows the result of the optimal antibody-pairing experiment.

1.7.2 the Test for Clinically Verifying the Optimal Antibody Pairs 3 pairs of gastric cancer keratin 18-highly related antibody pairs 3A9/2A6-HRP, 2A6/3A9-HRP, 3H7/3A9-HRP were preliminarily selected from the above cross antibody pairing test, and subjected to the clinical verification by using the ELISA method. A 96-well plate was coated with 1 µg/ml purified antibody and kept at 4° C. overnight, and then blocked with PBS containing 3% BSA at room temperature for 1 h. 10 gastric cancer samples and 10 normal human serum samples, 50 µl each, were taken as detection samples, and then added 50 µl of 1:1000 enzyme-labelled antibody. The plates were incubated at 37° C. and then washed, added a developing substrate, kept in the darkness for 10 min, added a stop solution, and measured for the OD value at 450 nm. The detection data were plotted as scatter points, and the diagnosis sensitivity and specificity were preliminarily observed and compared, as shown in FIG. 6.

The results showed that, in the 3A9/2A6-HRP detection, all of the gastric cancer serum detection values were higher than the normal human serum detection values, and both the sensitivity and the specificity were 100%; in the 2A6/3A9-HRP detection, 1 gastric cancer serum detection values were in the range of normal human serum detection values, the sensitivity and the specificity were lower than the former; in the 3H7/3A9-HRP detection, 4 gastric cancer serum detection values were in the range of normal human serum detection values, and the sensitivity and the specificity were lower than the two formers. Therefore, 3A9/2A6-HRP pair had the best serum diagnosis performance.

1.8 Study on the Characteristics of Tumor-Related Keratin 18 Monoclonal Antibodies 1.8.1 Determination of Tumor-Related Keratin 18 Fragment Antigen Determinant Recognized by the Antibody In order to further determine the antigen binding epitopes of 3A9 and 2A6, a group of recombinant keratin 18 fragments were prepared, and these fragments were truncated by ascending 50-amino acid deletion, as shown in Table 1-4. The binding activities of the antibodies to these antigens were measured by indirect ELISA method.

(1) ELISA microwell plates were coated with 1 µg/ml of various cytokeratin 18 fragments, and kept at 4° C. overnight;

(2) Washed with PBS three times, blocked with PBS containing 3% (w/v) BSA, and kept at room temperature for 1 h;

(3) To each of wells was added the detecting antibody (final concentration 1 µg/ml) and incubated at 37° C. for 1 h;

(4) Washed with PBS three times to remove the unbound antibodies. Then anti-mouse IgG antibody (µg/ml) conjugated with HRP was added, and incubated at 37° C. for 30 min;

(5) Washed with PBS three times, added the TMB substrate, standed for 10 min, then added the stop solution 2N $H_2SO_4$; and the sample wells were detected for light density at 450 nm/650 nm on the ELISA microplate reader.

TABLE 1-4

Determination of epitopes on antigen

| No. | Antigen | 3A9 | 2A6 |
| --- | --- | --- | --- |
| C1 | aa1-430 | + | + |
| C2 | aa50-430 | + | + |
| C3 | aa100-430 | + | + |
| C4 | aa150-430 | + | + |
| C5 | aa200-430 | + | + |
| C6 | aa250-430 | − | + |
| N7 | aa1-400 | + | + |
| N8 | aa1-350 | + | − |
| N9 | aa1-300 | + | − |
| N10 | aa1-250 | + | − |
|  |  | aa 200-250 | aa350-400 |

Figure 7:
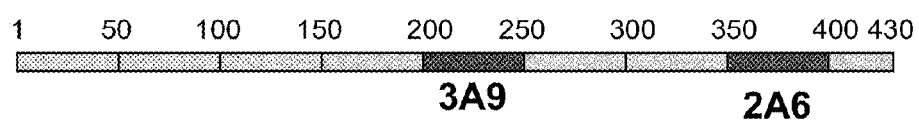
FIG. 7 is a schematic diagram, showing the positions of the binding epitopes of monoclonal antibodies 3A9 and 2A6.

The result showed that monoclonal antibody 3A9 bound the antigens 1-5, but could not bind the antigen 6 (aa250-430), and responded to all of C-terminal deleted fragments positively. Therefore, the antigen binding epitope of monoclonal antibody 3A9 was located in the cytokeratin 18 aa 200-250 fragment. Monoclonal antibody 2A6 responded to all of N-terminal deleted fragments positively and responded to one of N-terminal fragments (aa1-400) positively and to the other three N-terminal fragments negatively. Therefore the binding epitope of monoclonal antibody 2A6 was located in the cytokeratin 18 aa 350-400 fragment. The binding epitopes of monoclonal antibody 3A9 and the monoclonal antibody were shown in FIG. 7.

1.8.2 the Identification of the Type and the Subtype of the Antibodies Secreted by Hybridoma ELISA plates were coated with the purified keratin 18 antigens. To each well was added 100 μL of the cell supernatant of each of monoclonal antibodies, incubated at 37° C. for 30 min; washed on the full-automatic TECAN plate-washing machine with PBST for 5 times with an interval of 20 seconds, dried by striking, added a suitable dilution degree of HRP-goat antimouse IgM, IgG1, IgG2a, IgG2b, and IgG3 antibodies (Serotec Company) enzyme labeled secondary antibody, incubated at 37° C. for 30 min; washed on the full-automatic TECAN plate-washing machine with PBST for 5 times with an interval of 20 seconds, dried by striking, added the developing solutions A ($H_2O_2$) and B (TMB) each 1 drop, developed at 37° C. for 10 min, added 1 drop of stop solution (2M $H_2SO_4$); measured on the TECAN microplate reader for $OD_{450}$ nm (reference wavelength was 620 nm), the cutoff value was two times higher than the negative average. The OD value, if higher than the cutoff value, was positive, and the OD value, if smaller than the cutoff value, was negative. The result showed that 3A9 was IgG2a, and 2A6 was IgG1.

1.8.3 Specificity

Figure 8:
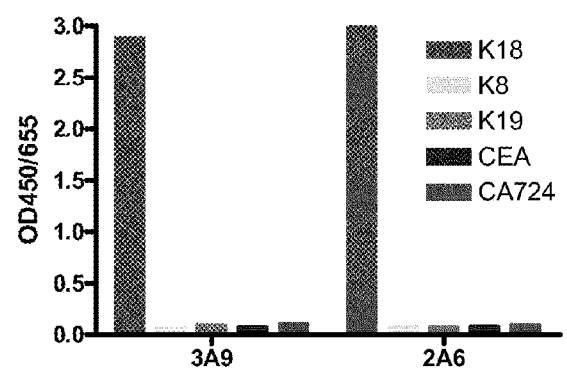
FIG. 8 shows the immunological detection result of monoclonal antibodies 3A9 and 2A6 and other human serum tumor markers.

In order to detect the reaction specificity of monoclonal antibodies 3A9 and 2A6, their immunobinding strength with other serum tumor markers were detected. Firstly 96-well plates were coated with K18, K8, K19, CEA, CA724 and other human serum tumor markers at 1 μg/ml, kept at 4° C. overnight, and then blocked with a PBS containing 3% BSA at room temperature for 1 h. In the detection, to each of wells were added 50 μl 1:1000 diluted monoclonal antibody 3A9 or 2A6; incubated at 37° C. for 30 min, washed with PBST washing solution for 5 times, after patting dry, peroxidase-conjugated goat antimouse IG (HRP-GAM Ig, DAKO Company) was added, incubated at 37° C. for 30 min, after removing the plate from the incubator, washed with PBST washing solution for 5 times, after patting dry, added successively the substrate solution A and the developing solution B, each 50 μl (the components of the substrate solution A were: 13.42 g $Na_2HPO_4.12H_2O$, 4.2 g citric acid.$H_2O$ and 0.3 g hydrogen peroxide, adjusted with deionized water to volume of 700 ml; the components of the developing solution B were: 0.2 g tetramethyl benzidine, 20 ml dimethylformamide adjusted with deionized water to volume of 700 ml), developed at 37° C. for 10 min, added 50 μl stop solution (2M $H_2SO_4$) to stop the reaction, and detected on the microplate reader for $OD_{450}$ values for each well. The result was shown in FIG. 8.

The result showed that the monoclonal antibodies 3A9 and 2A6 responded to K18 strongly positively, and responded to other tumor markers negatively. It was indicated that the monoclonal antibodies 3A9 and 2A6 were highly specific monoclonal antibodies of keratin 18.

2. Preparation for Keratin 18-3A9 Kit

The cytokeratin 18-3A9 test kit (chemiluminescence) was constituted by using a solid phase 96-well luminescent plate as reaction support, using a pair of gastric cancer-related anti-keratin 18 monoclonal antibodies to form a double antibody sandwich, and using highly sensitive chemiluminescence detection technique to quantitatively detect the keratin 18 fragments in gastric cancer patients' serum.

The K18 kit was prepared by using K18 monoclonal antibody 3A9 as coating antibody and K18 monoclonal antibody 2A6 as labeling antibody.

The main components of the kit comprised a standard substance, a coating plate, an enzyme conjugate, a luminescent solution, and a concentrated washing solution.

The standard substance was the purified keratin 18. The coating antibody was the K18 monoclonal antibody 3A9. The labeling antibody was the K18 monoclonal antibody 2A6. HRP horse radish peroxidase was used to label and form an antibody-HRP complex (enzyme conjugate).

The coating plate was prepared by coating with monoclonal antibody 3A9, washing, blocking, drying, and packaging in vacuum. The K18 monoclonal antibody 3A9 was coated at a coating concentration of 5 μg/mL in a citric acid buffer PH4.8 as coating buffer. The blocking solution was 0.02M PBS+0.4% casein+1% BSA+0.5M NaCl+0.2% gelatin+10% bovine serum+0.05% Tween-20+1% preservative+ 2.5% sucrose.

The labeling antibody was 2A6-HRP. The dilution solution was 0.02M PBS+1% casein+1% BSA+1% aminopyrin+ 0.05% Tween-20.

The luminescent solution was produced by splitting the luminescent solution A and luminescent solution B generated by KPL. The concentrated washing solution was 20×PBS washing solution.

3 Clinical Verification and Application

In the statistical analysis on the clinical trial, in view of the content of K18 in the serum of the patient in the convalescent period after treatment (chemotherapy and surgery) being remarkably reduced than that before the treatment, in order to exclude the interference caused by the treatment on the trial result, the serum samples of 24 first time gastric cancer patients (not treated), which were selected from 1000 clinical samples, were detected and analyzed. The result showed that the K18 kit had a sensitivity of 62.5%, and the CA72-4 kit had a sensitivity of 37.50%, as shown in details in Table 1-5.

TABLE 1-5

Comparison of K18 kit and CA72-4 kit on diagnosis and evaluation index for first time gastric cancer patients

| Diagnosing agent | Sensitivity % | Specificity % | Coincidence % | Positive prediction value % | Negative prediction value % |
|---|---|---|---|---|---|
| K18 | 62.50 | 96.00 | 92.41 | 65.22 | 95.52 |
| CA72-4 | 37.50 | 95.00 | 88.84 | 47.37 | 84.82 |

In the statistical analysis of the clinical trial, in view of the false positive rate of the diagnosis of the kit for the patients such as the patients with inflammation being an important factor on the diagnosis result, in this trial, comparative tests were conducted on the serum samples of 150 gastritis patients to compare the differential diagnosis capability of the K18 kit and the CA72-4 kit. The result showed that the K18 kit had a diagnosis false positive rate for the serum samples of the patients with inflammation of 5.3%, the CA72-4 kit had a diagnosis false positive rate for the serum samples of the patients with inflammation of 16.7%, and the K18 kit had a lower false positive rate than that of CA72-4, as shown in Table 1-6. The detection result showed that the present kit could distinguish very well the serum of the patients with inflammation from the serum of the patients with gastric cancer, and had an excellent specificity.

TABLE 1-6

The statistics of detection result from the serum of patients with inflammation

| Kit | Detection Result | |
|---|---|---|
| | Positive | Negative |
| K18 kit | 8 | 142 |
| CA72-4 kit | 25 | 125 |

Figure 9:
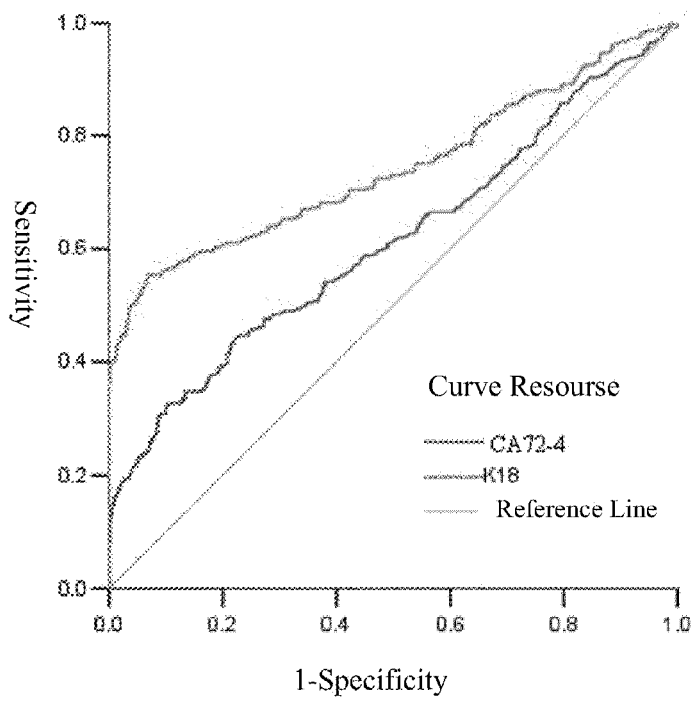
FIG. 9 shows the ROC curves for the diagnosis of gastric cancer and non-gastric cancer.

As shown in FIG. 9, it could be seen from the result of the analysis on the ROC curves that the area (0.743) under the ROC curve corresponding to the keratin 18-3A9 kit was larger than the area (0.612) under the ROC curve corresponding to the CA72-4 kit of Roche, therefore the keratin 18-3A9 kit has a better diagnosis result on gastric cancer than that of the CA72-4 kit.

In the pre-trial made at Cancer Hospital, Chinese Academy of Medical Sciences, a clinical verification pre-trial was conducted, in which 241 serum samples of cancer patients (84 samples for lung cancer; 76 samples for gastric cancer; and 81 samples for intestinal cancer), 61 samples of negative control (61 samples of serums from the normal human health examination) were selected. The result was shown in Table 1-7. It was indicated that the keratin 18-3A9 test kit (chemiluminescence) had a relatively high detection rate for other epithelium-derived tumors.

TABLE 1-7

The differential diagnosis result of K18 on various cancers

| | Sensitivity (%) | Specificity (%) |
|---|---|---|
| Lung cancer | 43 | 90 |
| Gastric cancer | 45 | 90 |
| Intestinal cancer | 53 | 90 |

Example 2

1 the Preparation of Monoclonal Antibodies Against Keratin 19 and its Fragments 1.1 Immunogen Recombinant cytokeratin 19 fragment GY20 was expressed in *E. coli* strain BL21(DE3).

Obtained by the following development scheme:

1.1.1 Research Scheme

Figure 10:
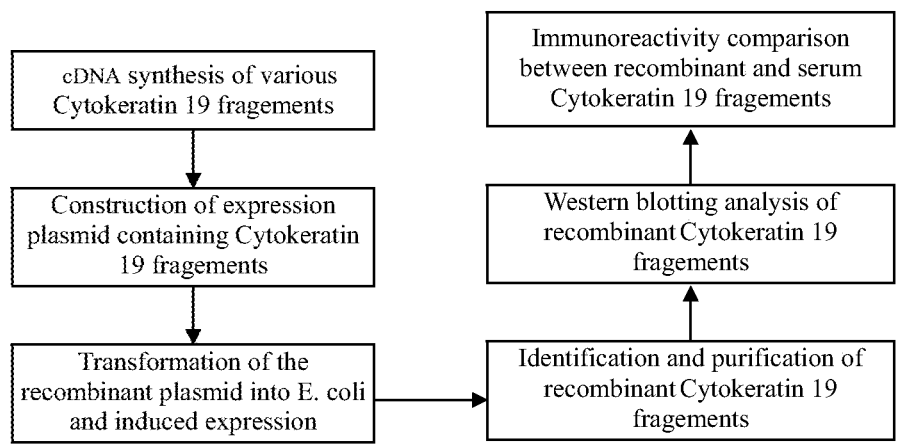
FIG. 10 is a flow chart, briefly describing the steps of preparing the cytokeratin 19 fragments and analyzing their activities.

See FIG. 10

1.1.2 the Synthesis of cDNA of Cytokeratin 19 Fragment cDNAs encoding various cytokeratin 19 fragments were prepared by the RT-PCR method a) Template and Primer Total RNAs were separated from a HELA human cancer cell line. Then, cDNAs were synthesized with the reverse transcription kit (Promega) according to its instruction. The obtained cDNAs were the templates for PCR. The primers were designed for three fragments, and each of cDNAs was subjected to the PCR amplification. Fragment numbers and amino acid sequences of the fragments were shown in Table 2-1.

TABLE 2-1

No. and amino acid sequence of recombinant cytokeratin 19 fragments

| No. of fragments | Amino acid sequence of cytokeratin 19 fragments |
|---|---|
| GY20 | aa1-400 |
| GY21 | aa150-400 |
| GY22 | aa200-400 | b) PCR Reaction

Components of PCR Reaction Solution:

cDNA template: 5 µl;

Primer: 5' and 3' primers, 10 pmol each

10×PCR buffer: 10 µl;

dNTP: 2.5 mM each, 4 µl in total;

Taq polymerase (Promega): 5 µl;

Sterile double distilled water, added to 100 µl.

Figure 11:
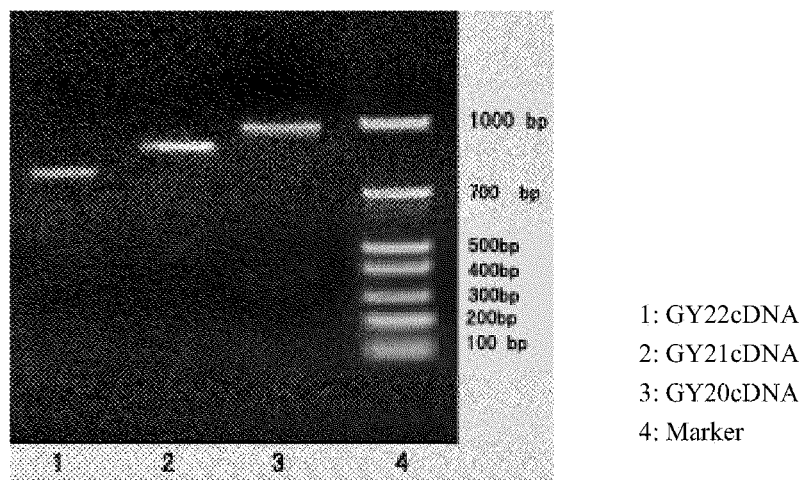
FIG. 11 is an electrophoretogram, showing the electrophoresis result of the cDNA of cytokeratin 19 fragments.

The Procedure was as Follows:

The solution was heated to 94° C., kept constantly for 2 min, then run for 40 cycles, wherein each cycle was set as follows: heated at 94° C. for 30 s, at 52° C. for 1 min, and at 72° C. for 3 min. After that, the reaction solution was heated to 72° C. for 10 min. Then the amplified DNA fragment was collected, and separated with 1% agarose gel containing 0.25 µg/ml ethidium bromide (See FIG. 11). The result showed that the bands contained the cDNA fragments of the desired cytokeratin 19 fragments. Then the DNA fragments were recovered with Gene Clean kit (BIO101, Irvine, Calif.).

1.1.3 Plasmid Construction and Screening

The cDNA fragment was cloned with TOPO100 expression Cloning Kit (Invitrogen, Carlsbad, Calif.).

Figure 12:
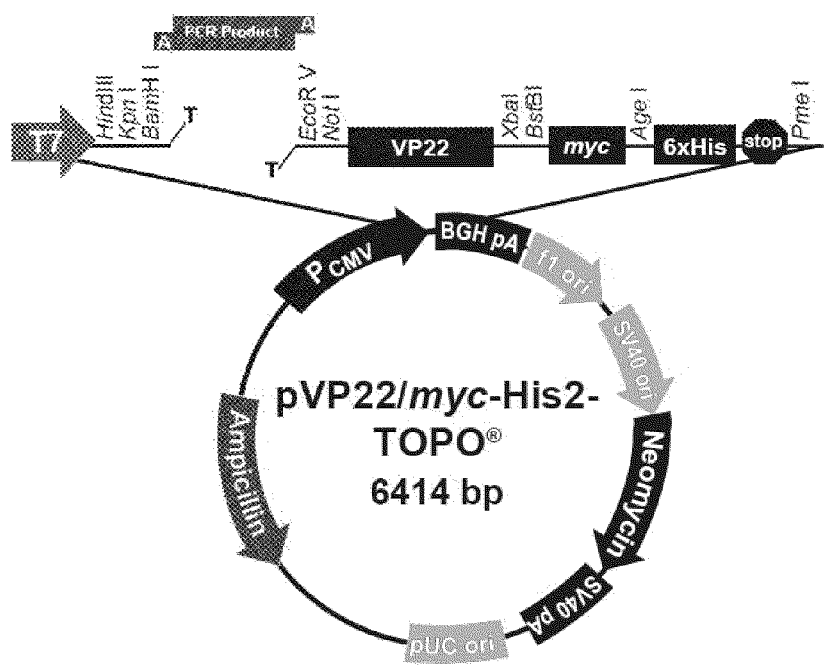
FIG. 12 shows the structure of the TOPO plasmid.

(11) The cDNA of cytokeratin 19 recovered from the PCR reaction solution and TOPO plasmid (FIG. 12) 50 ng provided from the cloning kit were mixed;

(12) To the solution was added 10× ligase reaction buffer (6 mM Tris-HCl (pH7.5), 6 mM MgCl, 5 mM NaCl, 7 mM β-mercaptoethanol, 0.1 mM ATP, 2 mM DTT, 1 mM spermidine, 0.1 mg/ml BSA);

(13) Then added 4 U T4 DNAligase (1 µl);

(14) The solution volume was adjusted with sterile deionized water to 10 µl;

(15) Incubated at 14° C. for 15 h;

(16) 2 µl was taken and added to 50 µl competent *E. coli* bacteria strain TOP10F (provided from TA cloning kit, and prepared into competence according to the instruction, the mixture was kept in an ice-bath for 30 min, then incubated at 42° C. for 30 s, and then in an ice-bath for 5 min)

(17) 500 µl of medium was formulated, containing 2% (v/v) peptone, 0.5% (w/v) yeast extract, 0.05% (w/v) NaCl, 2.5 mM KCl, 1 mM MgCl and 20 mM glucose, (6) was added thereto, and incubated at 37° C. for 1 h in shaking.

(18) On the L-broth agar plate (1% (v/v) peptone, 0.5% (w/v) yeast extract, 0.5% (w/v) NaCl, 0.1% glucose, 0.6% (w/v) bacto-agar (Difo, Detroit, Mich.)) was plated (7), 100 µg/ml.

(19) The clones resistant to Ampicillin could be screened out from the medium surface, a single colony was picked out with a Pt-coated coil, put into the L-broth medium (containing Ampicillin 100 μg/ml), incubated at 37° C. overnight in shaking (200 rpm).

(20) After the incubation, the bacteria were collected by centrifugation, and the DNA plasmid was extracted with alkaline process.

Figure 13:
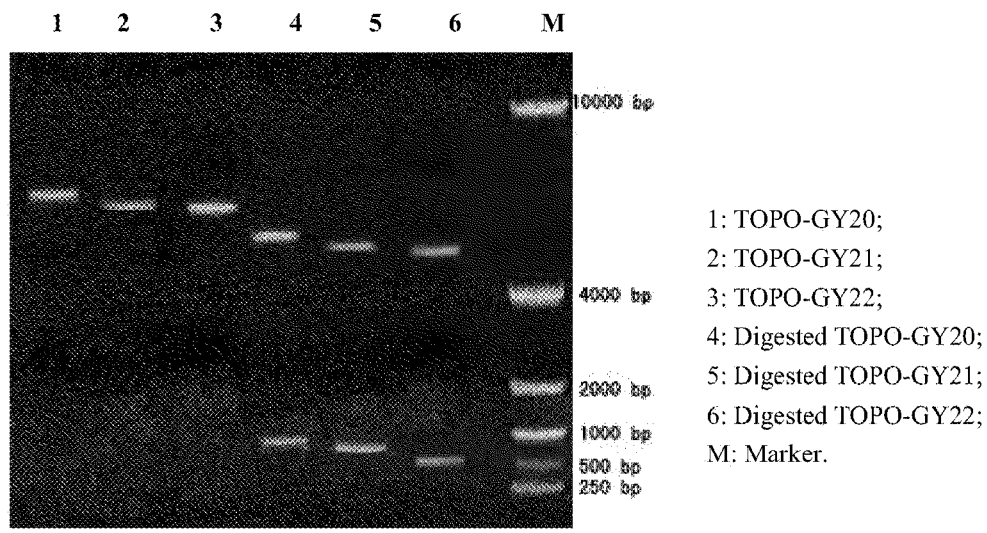
FIG. 13 is an electrophoretogram, showing the identification results of enzyme-digested recombinant expression plasmids TOPO-GY20, TOPO-GY21, and TOPO-GY22.

With the identification by enzyme digestion, the recombinant expression plasmids TOPO-GY20, TOPO-GY21, TOPO-GY22 had been obtained, as shown in FIG. 13.

1.1.4 Induced Expression and Identification of Recombinant Proteins cDNAs encoding various cytokeratin 19 had been inserted into TOPO plasmids, (5) The obtained plasmids were transformed into *E. coli* strains BL21(DE3), then cultured in LB medium to the index growth phase, and the expression was induced with isopropanol-β-thiogalactoside (IPTG) for 3 h.

(6) The cells were precipitated, resuspended with lysis solution (8M urea, 20 mM Tris-HCl), and disrupted ultrasonically.

(7) After centrifuged at 14,000×g for 15 min, the supernatant was purified on the Ni column. The purified protein was dialyzed with a PBS solution and kept at 4° C. overnight.

(8) The protein concentration was detected with a BCA agent (Pierece, Woburn, Mass.).

1.1.5 Purification of Recombinant Cytokeratin 19

Sephadex G-50 was activated, and recombinant cytokeratin 19 fragments were purified with sieve chromatography. Sephadex G-50 was dissolved in 100 mM Tris-HCl buffer (pH 7.4), boiled at 100° C. for 10 minutes, then blocked with 100 mM Tris-HCl buffer (pH 7.4), and stored at 4° C. The concentrated solution of disrupted bacteria flowed through 2 ml gel beads at a flow rate of 2 ml/min. After passed, the sample was rinsed with 50 ml PBS, and elution buffer was 0.1 M glycine (pH 2.4), 0.15 M NaCl. The eluate was measured at ultraviolet OD280 nm and judged whether the elution was complete. The effective eluate (OD>0.01) was collected, put in a dialysis bag, and dialyzed with 1 L phosphate buffer (pH7.5) at 4° C., during which the dialysis buffer was exchanged twice. The purified protein was concentrated to about 1 mg/ml, added 1% $NaN_3$, and stored at 4° C. It was detected with 10% SDS-PAGE, and scanned and analyzed with the GDS8000 gel imaging system for the protein purity.

Figure 14:
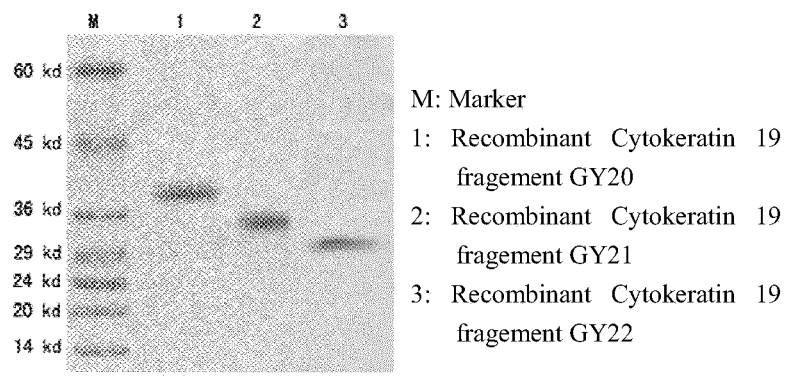
FIG. 14 is an electrophoretogram, showing the SDS-PAGE results of the recombinant cytokeratin 19 fragments GY20, GY21, and GY22.

The result was shown in FIG. 14. The result showed that high-purity recombinant cytokeratin 19 fragments GY20, GY21 and GY22 were obtained with an electrophoresis measured purity of over 95%.

The immunogen for preparing monoclonal antibodies was a full-length recombinant human cytokeratin 19, and this protein was bestowed by Prof. Zhou Tong, UAB university, US.

1.2 Immunization Procedure

Animal: 6-8 week-age female Balb/c mice.

Primary immunization (on Day 1): emulsified particles formed by evenly mixing 1 ml antigen protein solution and the same volume of Freund's complete adjuvant were used, with 100 μl plantar injection for each animal.

Secondary immunization (on Day 7): emulsified particles formed by evenly mixing 1 ml antigen protein solution and the same volume of Freund's incomplete adjuvant were used, with 100 μl plantar injection for each animal.

Enhanced immunization (on Days 14, 21 and 28): antigen (1 mg/ml) without any adjuvant was used, with 100 μl plantar injection for each animal.

Fusion (on Day 31).

1.3 Establishment of Hybridoma

Popliteal fossa and inguina of immuned mice were taken to separate lymphocytes which were mixed with NS1 myeloma cells at a ratio of 2:1. The mixture was washed with serum-free RPMI 1640 twice, and added 1 ml PEG1500 (preheated to 37° C.); the cells were mixed slightly at 37° C. for 1 min, then added dropwise slowly 20 ml serum-free RPMI 1640 medium (preheated to 37° C.) within 3 minutes. After centrifugation, the fused cells were suspended in 12% FBS RPMI 1640 HAT selective medium. Cells were put in five 96-well cell culture plates, 100 μl/well.

1.4 Screening Positive Clones by ELISA Assay

On Day 7 after the cell fusion, the primary screening was conducted by indirect ELISA method. All of the hybridomas were screened with three recombinant human cytokeratin 19 antigens: (1) full-length cytokeratin 19; (2) N-terminal cytokeratin 19 fragment; and (3) C-terminal cytokeratin 19 fragment.

The ELISA plates were coated with the above keratin 19 antigens (1 μg/ml) at 4° C. overnight; washed with PBS three times, and blocked with PBS containing 3% (w/v) BSA at room temperature for 1 h. When detecting, 100 μl supernatant of the cell culture was added to each well; incubated at 37° C. for 30 min, washed with PBST washing solution for 5 times, after patting dry, peroxidase-conjugated goat antimouse immunoglobulin (HRP-GAM Ig, DAKO Company) was added, incubated at 37° C. for 30 min, after removing the plate from the incubator, washed with PBST washing solution for 5 times, after patting dry, added successively the substrate solution A and the developing solution B, each 50 μl (the components of the substrate solution A were: 13.42 g $Na_2HPO_4.12H_2O$, 4.2 g citric acid.$H_2O$ and 0.3 g hydrogen peroxide, adjusted with deionized water to volume of 700 ml; the components of the developing solution B were: 0.2 g tetramethyl benzidine, 20 ml dimethylformamide adjusted with deionized water to volume of 700 ml), developed at 37° C. for 10 min, added 50 μl stop solution (2M $H_2SO_4$) to stop the reaction, and detected on the microplate reader for $OD_{450}$ values for each well, wherein those having a $OD_{450}$ value higher than 2.0 were regarded as positive.

The result of the primary screening of the monoclonal antibodies was summarized in Table 2-2. After detecting the supernatants resulted from the hybridoma culture in all of 480 wells with four antigens, the inventors identified that 39 clones had strong responses with the full-length cytokeratin 19 antigen, wherein 3 clones showed positive responses with the N-terminal and C-terminal fragments of keratin 19 and irrelevant control antigen, which were regarded as nonspecific clones; wherein 15 clones showed positive responses with the N-terminal cytokeratin 19 fragments, and defined as N-terminal specific clones; wherein 18 clones showed positive responses with the C-terminal cytokeratin 19 fragments, and defined as C-terminal specific clones. In addition, three clones responded to the N-terminal and C-terminal antigens, and their response specificity was unknown. These N-terminal and C-terminal specific clones were used as candidates for further study.

These clones were subjected to three sub-clonings by the limiting dilution assay.

TABLE 2-2

The result of the primary screening for mouse anti-human keratin 19 monoclonal antibodies

| | Response Result | | | 480 clones in total the number of positive clones | Note |
|---|---|---|---|---|---|
| full-length keratin 19 | N-terminal fragment (aa1-250) | C-terminal fragment (aa150-400) | control antigen | | |
| + | + | + | + | 3 | non-specific |
| + | + | − | − | 15 | N-terminal-specific |
| + | − | + | − | 18 | C-terminal-specific |
| + | + | + | − | 3 | unknown |

1.5 the Production and Purification of Monoclonal Antibodies 16 week-age healthy Balb/c mice were injected intraperitoneally with 0.5 ml pristane. 5-7 days later, clonized hybridoma cells were collected, centrifuged to remove the supernatant, added a serum-free medium, adjusted to cell density of $2×10^5$-$2×10^6$ cells/ml, each of mice was injected with 0.5 ml. 7-10 days later, the abdomen of mice enlarged, and the collection of ascites began. After centrifuging at 3000 rpm for 15 min, the intermediate pellucid liquid was taken, filtered with 0.45 μm micropore film to remove bacteria, separately packaged, and stored at −20° C.

The treated ascites was 5-fold diluted with 0.02 mol/L, pH7.4 PBS (81 ml 0.2 mol/L $Na_2HPO_4$, 19 ml 0.2 mol/L $NaH_2PO_4$, added to 100 ml with physiological saline). 50 ml supernatant was added to 2 ml protein-A/G chromatography column at a flow rate of 1 ml/min. Then the affinity chromatography column was washed with PBS until the effluent had an OD280 value of below 0.01. Then the antibodies bound to the chromatography column were eluted with 0.1M Glycine-HCL buffer pH2.4, the eluted components were collected in 2 ml/tube, finally all of the eluted components having OD280 higher than 0.1 were mixed, then neutralized with 1/10 volume of 1M Tris-HCL pH 8.5 solution, and then dialyzed overnight in the PBS solution, during which the dialysis buffer was exchanged twice.

1.6 The Preparation of Enzyme Labelled Antibody

The conventional method for labeling the monoclonal antibody and the polyclonal antibody with horse radish peroxidase (HRP) was sodium periodate method. Its principle was that the glycosyl of HRP was oxidized with sodium periodate to become an aldehyde group, after adding the antibody IgG, the aldehyde group bound with the amino of IgG to form a Schiff base. In order to prevent the aldehyde group of the saccharide in the HRP from coupling with the amino of the protein itself, the amino was blocked with dinitrofluorobenzene before the oxidation with sodium periodate. At the end of the oxidation reaction, the Schiff base was stabilized with sodium borohydride.

(1) Dissolving 5 mg HRP into 0.5 ml 0.1 mol/L $NaHCO_3$ solution; adding 0.5 ml 10 mmol/L $NaIO_4$ solution, mixing evenly, closing the lid tightly, keeping at room temperature in the darkness for 2 h.

(2) Adding 0.75 ml 0.1 mol/L $Na_2CO_3$ and mixing evenly.

(3) Adding 0.75 ml purified monoclonal antibody (15 mg/ml), and mixing evenly.

(4) Weighing Sephadex G25 dried powder 0.3 g, adding to the outer barrel of 5 ml syringe matted with glass cotton at the lower opening; then transferring the above conjugate into the syringe outer jacket; closing tightly, keeping at room temperature (in the darkness) for 3 h or at 4° C. overnight.

(5) Eluting all of the conjugate with a small amount of PBS, collecting the eluate, adding 1/20V-volumed fresh 5 mg/ml $NaBH_4$ solution, mixing evenly, keeping at room temperature for 30 min; Then adding 3/20V $NaBH_4$ solution, mixing evenly, keeping at room temperature for 1 h (or at 4° C. overnight).

(6) Passing the conjugate through Sephadex G200 or Sepharose 6B (2.6×50 cm) to purify by chromatography, and collecting the first peak in separate tubes.

(7) Identifying the mass of enzyme conjugate:
Determination of Molar Ratio
Enzyme amount (mg/ml)=$OD_{403}×0.4$
IgG amount (mg/ml)=$(OD_{280}−OD_{403}×0.3)×0.62$
Molar ratio (E/P)=Enzyme amount×4/IgG amount, generally between 1 and 2.

Enzyme binding rate=enzyme amount×volume/antibodies. The labeling rate is generally 0.3-0.6, i.e. 1-2 HRP molecules may bind to one antibody molecule. The labeling rate can be higher than 0.6, 0.8, 0.9; When $OD_{403}/OD_{280}$ equals to 0.4, E/P is about 1.

The labeling rate=$OD_{403}/OD_{280}$

Determination of Enzyme Activity and Antibody Activity

The enzyme activity of the enzyme conjugate, antibody activity, titer and specificity could be determined by ELISA method, immunodiffusion, DAB-$H_2O_2$ chromogenic reaction.

(8) Preserving the HRP antibody conjugate: adding glycerol of the same amount, splitting into small amounts and keeping at −20° C. so as to avoid repeated freezing and thawing; or adding the same amount of 60% glycerol and keeping at 4° C.; it was not suitable to add $NaN_3$ or phenol for antisepsis, otherwise the enzyme activity would be compromised. If necessary, preserving under lyophilization, with BSA or skim milk as protector.

1.7 Screening for Tumor-Related Keratin 19 Fragment Monoclonal Antibody Pairs

After confirming the antigen reactivities of purified and enzyme labelled antibodies by ELISA method, 10 strains of antibodies with high affinity were selected to conduct the paring test to screen out lung cancer-highly related keratin 19 antibody pairs.

1.7.1 Cross-Pairing Test Design

In order to obtain monoclonal antibody pairs having selectivity to lung cancer serum keratin 19, 10 lung cancer serum samples and 10 normal human serum samples were taken as testing samples. 10 lung cancer serum samples of the same volume were mixed as the positive sample. 10 normal human serum samples of the same volume were mixed as the negative sample. A 96-well plate was coated with 1 μg/ml purified antibody and kept at 4° C. overnight, and then blocked with a PBS containing 3% BSA at room temperature for 1 h. Then, to each well of one ELISA plate was added 50 μl of lung cancer positive serum, and to each well of another ELISA plate was added the normal human negative control serum, and then 50 μl of 1:1000 enzyme labelled antibodies were added respectively. The plates were incubated at 37° C. and then washed, added a developing substrate, kept in the darkness for 10 min, added a stop solution, and measured for the OD value at 450 nm.

Table 2-3 summarized the cross-pairing test results for 5 pairs of monoclonal antibodies, wherein 2G2/5H2-HRP, 5H2/2G2-HRP, 5H2/1D11-HRP antibody pairs showed strong positive responses to lung cancer serum and negative responses to normal human serum. Therefore, it was established that the serum keratin 19 detected by these antibody pairs are highly related to lung cancer.

TABLE 2-3

Crossing test for screening lung cancer-related keratin 19 antibody

| | | Coating antibody | | | | |
|---|---|---|---|---|---|---|
| Normal human | Lung cancer | 1D11 | 1H5 | 2G2 | 4C9 | 5H2 |
| Enzyme-labeled antibody | 1D11 | 0.09 | 0.06 | 0.07 | 0.08 | 0.08 |
| | | 0.08 | 0.31 | 1.28 | 0.44 | 1.44 |
| | 1H5 | 0.05 | 0.11 | 0.06 | 0.1 | 0.07 |
| | | 0.23 | 0.09 | 1.42 | 0.22 | 1.25 |
| | 2G2 | 0.06 | 0.08 | 0.08 | 0.08 | 0.06 |
| | | 0.44 | 0.32 | 0.12 | 1.32 | 1.98 |
| | 4C9 | 0.08 | 0.1 | 0.11 | 0.07 | 0.08 |
| | | 0.54 | 0.22 | 1.26 | 0.09 | 0.54 |
| | 5H2 | 0.09 | 0.08 | 0.08 | 0.08 | 0.08 |
| | | 1.12 | 0.98 | 2.48 | 0.66 | 0.12 |

Figure 15:
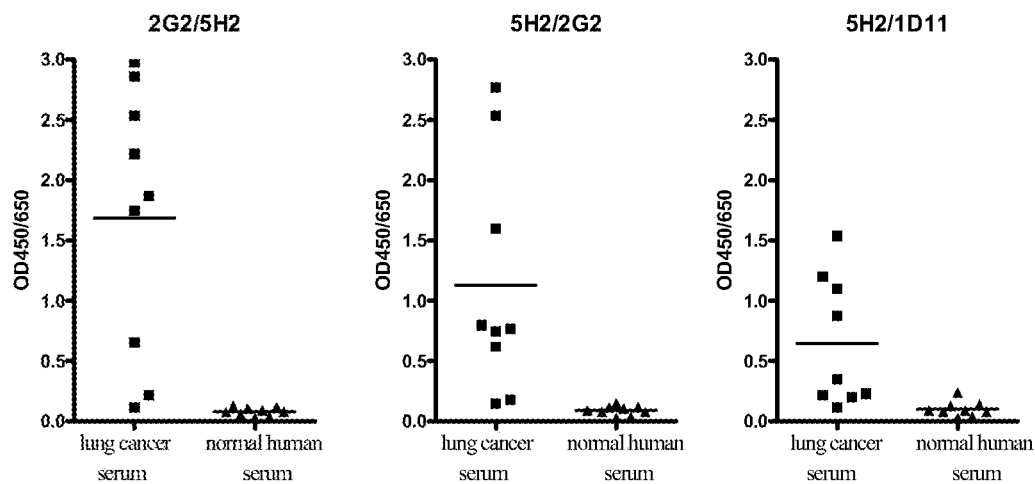
FIG. 15 shows the result of the optimal antibody-pairing experiment.

1.7.2 the Test for Preliminarily Verifying the Optimal Antibody Pairs 3 pairs of lung cancer keratin 19-highly related antibody pairs 2G2/5H2-HRP, 5H2/2G2-HRP, 5H2/1D11-HRP were preliminarily selected from the above cross antibody pairing test, and subjected to the clinical verification by using the ELISA method. A 96-well plate was coated with 1 μg/ml purified antibody and kept at 4° C. overnight, and then blocked with a PBS containing 3% BSA at room temperature for 1 h. 10 lung cancer serum samples and 10 normal human serum samples, 50 μl each, were taken as detection samples, and then added 50 μl of 1:1000 enzyme-labelled antibody. The plates were incubated at 37° C. and then washed, added a developing substrate, kept in the darkness for 10 min, added a stop solution, and measured for the OD value at 450 nm. The detection data were plotted as scatter points, and the diagnosis sensitivity and specificity were preliminarily observed and compared, as shown in FIG. 15.

The results showed that in the 2G2/5H2-HRP detection, 1 lung cancer serum detection value was in the range of normal human serum detection values, and other lung cancer serum detection values were higher, if taking the specificity as 100%, the sensitivity was 90%; in the 5H2/2G2-HRP detection, 2 lung cancer serum detection values were in the range of normal human serum detection values, 4 lung cancer serum detection values were relatively low, if taking the specificity as 100%, the sensitivity was 80%; in the 5H2/1D11-HRP detection, 4 lung cancer serum detection values were in the range of normal human serum detection values, and all of lung cancer serum detection values were lower than the two former, if taking the specificity as 100%, the sensitivity was 60%. Therefore, 2G2/5H2-HRP pair had the best serum diagnosis performance.

1.8 Study on the Characteristics of Tumor-Related Keratin 19 Monoclonal Antibodies 1.8.1 Determination of Tumor-Related Keratin 19 Fragment Antigen Determinant In order to further determine the antigen binding epitopes of 2G2 and 5H2, a group of recombinant keratin 19 fragments were prepared, and these fragments were truncated by ascending 50-amino acid deletion, as shown in Table 2.4. The binding activities of the antibodies to these antigens were measured by indirect ELISA method.

(1) ELISA microwell plates were coated with 1 μg/ml of various cytokeratin 19 fragments, and kept at 4° C. overnight;

(2) Washed with PBS three times, blocked with PBS containing 3% (w/v) BSA, and kept at room temperature for 1 h;

(3) To each of wells was added the detecting antibody (final concentration 1 μg/ml) and incubated at 37° C. for 1 h;

(4) Washed with PBS three times to remove the unbound antibodies. Then anti-mouse IgG antibody (μg/ml) conjugated with HRP was added, and incubated at 37° C. for 30 min;

(5) Washed with PBS three times, added the TMB substrate, standed for 10 min, then added the stop solution 2N $H_2SO_4$; and the sample wells were detected for light density at 450 nm/650 nm on the ELISA microplate reader.

TABLE 2-4

Determination of epitope on antigen

| No. | Antigen | 2G2 | 5H2 |
|---|---|---|---|
| C1 | aa1-400 | + | + |
| C2 | aa50-400 | + | + |
| C3 | aa100-400 | + | + |
| C4 | aa150-400 | + | + |
| N5 | aa1-375 | − | + |
| N6 | aa1-350 | − | − |
| N7 | aa1-300 | − | − |
| N8 | aa1-250 | − | − |
| | | aa 375-400 | aa325-350 |

Figure 16:
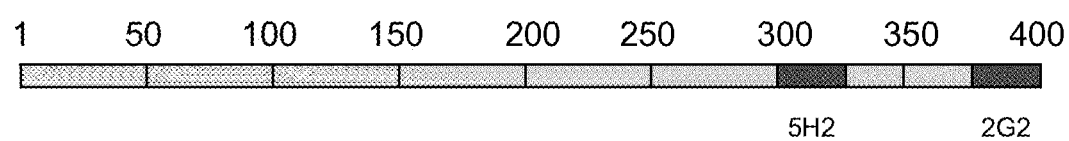
FIG. 16 is a schematic diagram, showing the positions of the binding epitopes of monoclonal antibodies 2G2 and 5H2.

The result showed that monoclonal antibody 2G2 bound antigens 1-4, and responded to all of C-terminal deleted fragments positively. Therefore, the antigen binding epitope of monoclonal antibody 2G2 was located in the cytokeratin 19 aa 375-400 fragment. The monoclonal antibody 5H2 responded to all of N-terminal deleted fragments positively, and responded to 1 N-terminal fragment (aa1-375) positively, and to other three N-terminal fragments negatively. The binding epitope of monoclonal antibody 5H2 was located in the cytokeratin 19 aa 325-350 fragment. The binding epitopes of monoclonal antibody 2G2 and monoclonal antibody 5H2 were shown in FIG. 16.

1.8.2 the Identification of the Type and Subtype of the Antibodies Secreted by Hybridoma ELISA plates were coated with the purified keratin 19 antigens. To each well was added 100 μL of the cell supernatant of each of monoclonal antibodies, incubated at 37° C. for 30 min; washed on the full-automatic TECAN plate-washing machine with PBST for 5 times with an interval of 20 seconds, dried by striking, added a suitable dilution degree of HRP-goat antimouse IgM, IgG1, IgG2a, IgG2b, and IgG3 antibodies (Serotec Company) enzyme labeled secondary antibody, incubated at 37° C. for 30 min; washed on the full-automatic TECAN plate-washing machine with PBST for 5 times with an interval of 20 seconds, dried by striking, added the developing solutions A ($H_2O_2$) and B (TMB) each 1 drop, developed at 37° C. for 10 min, added 1 drop of stop solution (2M $H_2SO_4$); measured on the TECAN microplate reader for $OD_{450}$ nm (reference wavelength was 620 nm), the cutoff value was two times the negative average. The OD value, if higher than the cutoff value, was positive, and the OD value, if smaller than the cutoff value, was negative. The result showed that 2G2 was IgG2a, and 5H2 was IgG1.

1.8.3 Specificity

Figure 17:
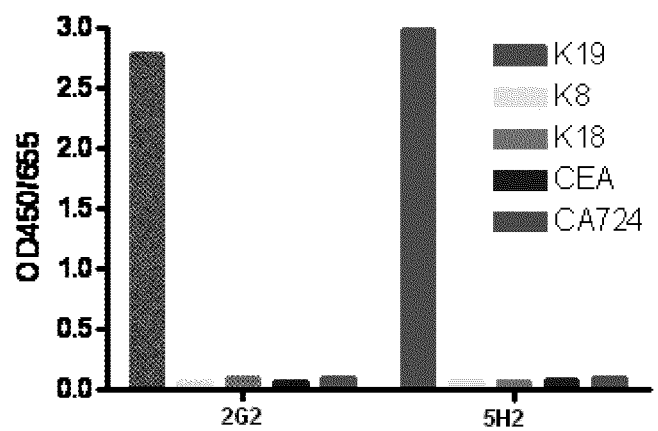
FIG. 17 shows the immunological detection result of monoclonal antibodies 2G2 and 5H2 and other human serum tumor markers.

In order to detect the reaction specificity of monoclonal antibodies 2G2 and 5H2, their immunobinding strength with other serum tumor markers were detected. Firstly 96-well plates were coated with K18, K8, K19, CEA, CA724 and other human serum tumor markers at 1 µg/ml, kept at 4° C. overnight, and then blocked with a PBS containing 3% BSA at room temperature for 1 h. In the detection, to each of wells were added 50 µl 1:1000 diluted monoclonal antibody 2G2 or 5H2; incubated at 37° C. for 30 min, washed with PBST washing solution for 5 times, after patting dry, peroxidase-conjugated goat antimouse IG (HRP-GAM Ig, DAKO Company) was added, incubated at 37° C. for 30 min, after removing the plate from the incubator, washed with PBST washing solution for 5 times, after patting dry, added successively the substrate solution A and the developing solution B, each 50 µl (the components of the substrate solution A were: 13.42 g $Na_2HPO_4.12H_2O$, 4.2 g citric acid.$H_2O$ and 0.3 g hydrogen peroxide, adjusted with deionized water to volume of 700 ml; the components of the developing solution B were: 0.2 g tetramethyl benzidine, 20 ml dimethylformamide adjusted with deionized water to volume of 700 ml), developed at 37° C. for 10 min, added 50 µl stop solution (2M $H_2SO_4$) to stop the reaction, and detected on the microplate reader for $OD_{450}$ values for each well. The result was shown in FIG. 17.

The result showed that the monoclonal antibodies 2G2 and 5H2 responded to K19 strongly positively, and responded to other tumor markers negatively. It was indicated that the monoclonal antibodies 2G2 and 5H2 were highly specific monoclonal antibodies of keratin 19.

2 Preparation for Keratin 19-2G2 Kit

The cytokeratin 19-2G2 test kit (chemiluminescence) was constituted by using a solid phase 96-well luminescent plate as reaction support, using a pair of lung cancer-related anti-keratin 19 monoclonal antibodies to form a double antibody sandwich, and using highly sensitive chemiluminescence detection technique to quantitatively detect the keratin 19 fragments in lung cancer patients' serum.

The K19 kit was prepared by using K19 monoclonal antibody 2G2 as coating antibody and K19 monoclonal antibody 5H2 as labeling antibody.

The main components of the kit comprised a standard substance, a coating plate, an enzyme conjugate, a luminescent solution, and a concentrated washing solution. The standard substance was purified keratin 19. The coating antibody was K19 monoclonal antibody 2G2. The labeling antibody was K19 monoclonal antibody 5H2. HRP horse radish peroxidase was used to label and form an antibody-HRP complex (enzyme conjugate).

The coating plate was prepared by coating with monoclonal antibody 2G2, washing, blocking, drying, and packaging in vacuum.

K19 monoclonal antibody 2G2 was coated at a coating concentration of 5 µg/mL in a citric acid buffer PH4.8 as coating buffer.

The blocking solution was 0.02M PBS+0.4% casein+1% BSA+0.5M NaCl+0.2% gelatin+10% bovine serum+0.05% Tween-20+1% preservative+2.5% sucrose.

The labeling antibody was 5H2-HRP. The dilution solution was 0.02M PBS+0.4% casein+1% BSA+0.5M NaCl+1% aminopyrin+0.2% gelatin+10% bovine serum+0.05% Tween-20.

The luminescent solution was produced by separately packaging the luminescent solution A and luminescent solution B generated by KPL. The concentrated washing solution was 20×PBS washing solution.

3 Clinical Verification and Application

In the statistical analysis of clinical trial, in view of the content of K19 in the serum of patients in the convalescent period after treatment (chemotherapy and surgery) being remarkably reduced than that before the treatment, in order to exclude the interference caused by the treatment on the trial result, the serum samples of 69 first time lung cancer patients (not treated), which were selected from 1000 clinical samples, were detected and analyzed. The result showed that the K19 kit had a sensitivity of 88.4%, and the CYFRA21-1 kit had a sensitivity of 52.17%, as shown in Table 2-5.

TABLE 2-5

Comparison of K19 kit and CYFRA21-1 kit on diagnosis and evaluation index for first time lung cancer patients

| Diagnosing agent | Sensitivity % | Specificity % | Coincidence % | Positive prediction value % | Negative prediction value % |
|---|---|---|---|---|---|
| K19 | 88.41 | 97.50 | 95.17 | 92.42 | 96.06 |
| CYFRA21-1 | 52.17 | 95.50 | 84.39 | 80.00 | 85.27 |

In the statistical analysis of the clinical trial, in view of the false positive rate of the diagnosis of the kit for the patients such as patients with inflammation being an important factor on the diagnosis result, in this trial, comparative tests were conducted on the serum samples of 150 pneumonia patients to compare the differential diagnosis capability of the K19 kit and the CYFRA21-1 kit. The result showed that the K19 kit had a diagnosis false positive rate for the serum samples of the patients with inflammation of 5.3%, the CYFRA21-1 kit had a diagnosis false positive rate for the serum samples of the patients with inflammation of 12.0%, and the K19 kit had a lower false positive rate than that of CYFRA21-1, as shown in Table 2-6. The detection result showed that the present kit could distinguish very well the serum of the patients with inflammation from the serum of the patients with lung cancer, and had an excellent specificity.

TABLE 2-6

The statistics of detection result from the serum of patients with inflammation

| Kit | Detection Result | |
|---|---|---|
| | Positive | Negative |
| K19 kit | 8 | 142 |
| CYFRA21-1 kit | 18 | 132 |

Figure 18:
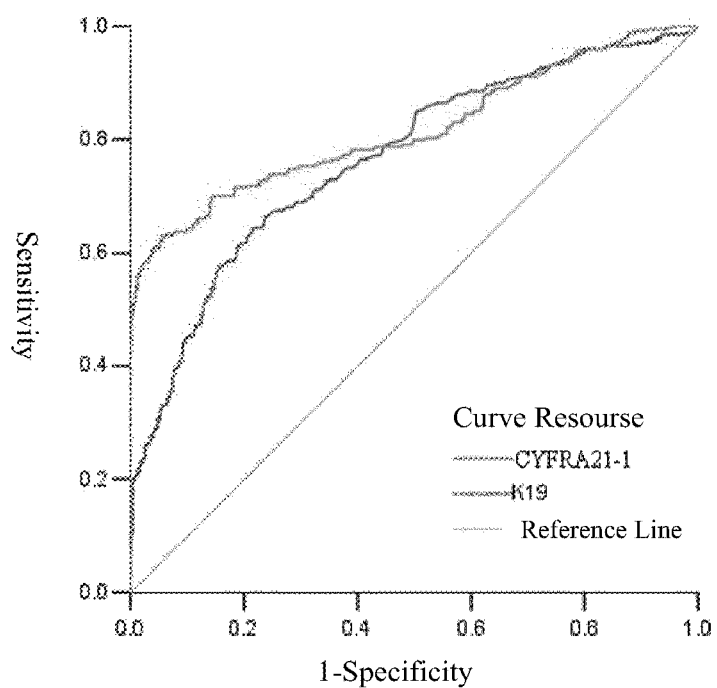
FIG. 18 shows the ROC curves for the differential diagnosis of lung cancer and non-lung cancer.

It could be seen from the result of the analysis on the ROC curves in FIG. 18 that the area (0.817) under the ROC curve corresponding to the keratin 19-2G2 kit was larger than the area (0.766) under the ROC curve corresponding to the CYFRA21-1 kit of Roche, therefore the keratin 19-2G2 kit has a better diagnosis result on lung cancer than the CYFRA21-1 kit.

In the pre-trial made at Cancer Hospital, Chinese Academy of Medical Sciences, a clinical verification pre-trial was conducted, in which 241 serum samples of cancer patients (84 samples for lung cancer; 76 samples for gastric cancer; and 81 samples for intestinal cancer), 61 samples of negative control (61 samples of serums from the normal human health examination) were selected. The result was shown in Table 2-7. It was indicated that the keratin 19-2G2 test kit (chemiluminescence) had a relatively high detection rate for other epithelium-derived tumors.

TABLE 2-7

The differential diagnosis result of K19 on various cancers

| Type | Sensitivity (%) | Specificity (%) |
|---|---|---|
| lung cancer | 75 | 90 |
| gastric cancer | 63 | 90 |
| intestinal cancer | 62 | 90 |

We claim:

1. A monoclonal antibody that specifically binds to an epithelium-derived cancer-related cytokeratin fragment, wherein the fragment comprises one or more epitopes selected from the group consisting of SEQ ID NOs: 2 and 3, wherein the antibody is produced by a hybridoma having a deposit number selected from the group consisting of CGMCC 1957 and CGMCC 1956.

2. The monoclonal antibody of claim 1, wherein the epithelium-derived cancer-related cytokeratin fragment comprises amino acid residues selected from the group consisting of amino acid residues 1-250 of SEQ ID NO: 1, amino acid residues 250-430 of SEQ ID NO: 1, and amino acid residues 150-430 of SEQ ID NO: 1.

3. The monoclonal antibody of claim 1, wherein the antibody comprises a chimeric antibody or a humanized antibody.

4. The monoclonal antibody of claim 1, wherein the epithelium-derived cancer-related cytokeratin fragment is associated with breast cancer, gastric cancer, oral cancer, esophageal cancer, colon cancer, liver cancer, bladder cancer, pancreatic cancer, ovarian cancer, cervical cancer, lung cancer, breast cancer, skin cancer, prostate cancer, or renal cancer.

5. A method of determining a diagnosis or prognosis of cancer in a subject, comprising contacting a biological sample from the subject with a monoclonal antibody that specifically binds to an epithelium-derived cancer-related cytokeratin fragment, wherein the fragment comprises one or more epitopes selected from the group consisting of SEQ ID NOs: 2 and 3, and wherein the antibody is produced by a hybridoma having a deposit number selected from the group consisting of CGMCC 1957 and CGMCC 1956.

6. The method of claim 5, wherein the epithelium-derived cancer-related cytokeratin fragment comprises amino acid residues selected from the group consisting of amino acid residues 1-250 of SEQ ID NO: 1, amino acid residues 250-430 of SEQ ID NO: 1, and amino acid residues 150-430 of SEQ ID NO: 1.

7. The method of claim 5, wherein the antibody comprises a chimeric antibody or a humanized antibody.

8. The method of claim 5, wherein the biological sample comprises blood, serum, tissue fluid, urine, excrement, sputum, cerebrospinal fluid, saliva, tears, or nipple aspirate fluid.

9. The method of claim 5, wherein the epithelium-derived cancer-related cytokeratin fragment is associated with breast cancer, gastric cancer, oral cancer, esophageal cancer, colon cancer, liver cancer, bladder cancer, pancreatic cancer, ovarian cancer, cervical cancer, lung cancer, breast cancer, skin cancer, prostate cancer, or renal cancer.

10. The method of claim 5, further comprising comparing the level of a subject's cytokeratin fragments to that of one or more other epithelium-derived tumor markers, wherein the other epithelium-derived tumor markers are selected from the group consisting of AFP, CEA, CA242, CA19-9, CA72-4, CA125, CA15-3, NSE, SCCA, Cyfra21-1, PSA, and free PSA.

11. The method of claim 5, further comprising contacting the sample with a monoclonal antibody produced by a hybridoma having a deposit number selected from the group consisting of CGMCC 1955 and CGMCC 1952.

12. A kit for determining a diagnosis or prognosis of cancer, comprising the monoclonal antibody of claim 1.

13. The kit of claim 12, wherein the epithelium-derived cancer-related cytokeratin fragment comprises amino acid residues selected from the group consisting of amino acid residues 1-250 of SEQ ID NO: 1, amino acid residues 250-430 of SEQ ID NO: 1, and amino acid residues 150-430 of SEQ ID NO: 1.

14. The kit of claim 12, wherein the monoclonal antibody comprises a chimeric antibody or a humanized antibody.

15. The kit of claim 12, further comprising an antibody produced by a hybridoma having a deposit number selected from the group consisting of CGMCC 1955 and CGMCC 1952.

16. A hybridoma cell line having a deposit number selected from the group consisting of CGMCC 1957 and CGMCC 1956.

* * * * *